Figure 2:
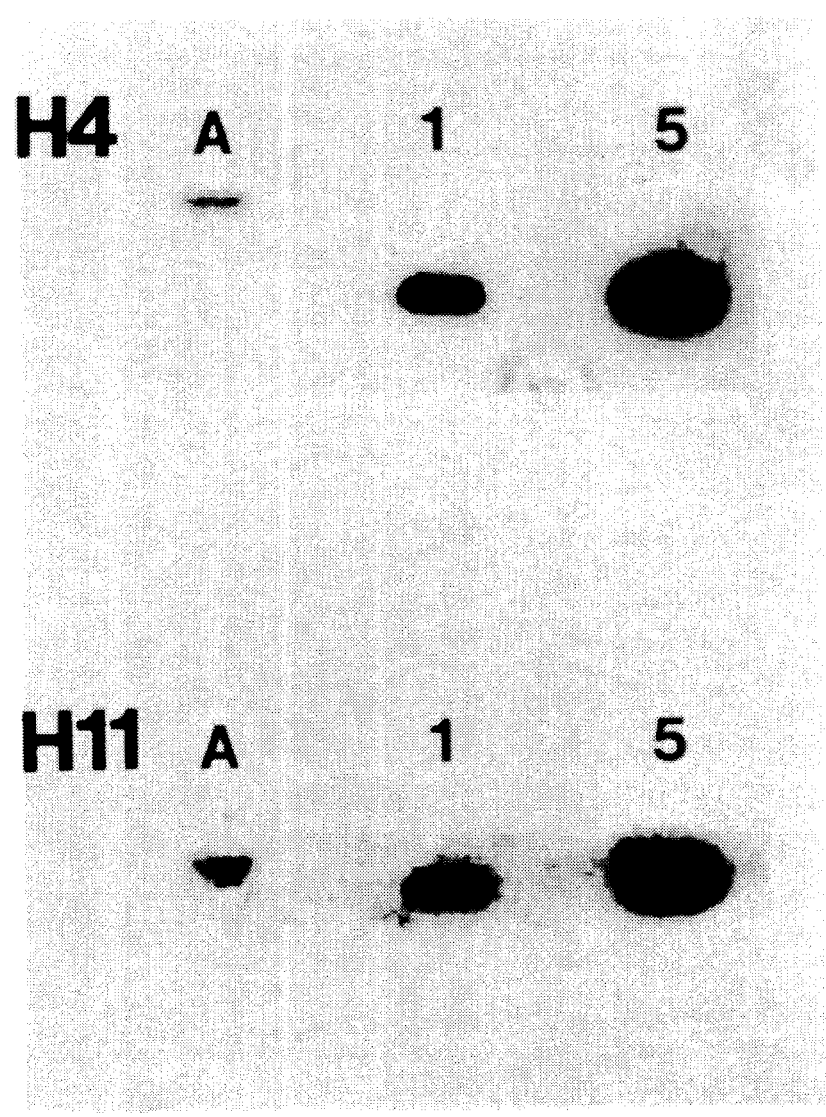

United States Patent [19]

McDonald et al.

[11] Patent Number: 5,578,453
[45] Date of Patent: Nov. 26, 1996

[54] CLONING AND EXPRESSION OF TOXOPLASMA ANTIGENS AND USE OF RECOMBINANT ANTIGENS

[75] Inventors: Peter J. McDonald, Belair; Alan M. Johnson, East Roseville, both of Australia

[73] Assignee: The Flinders University of South Australia, South Australia, Australia

[21] Appl. No.: 972,481

[22] PCT Filed: Aug. 9, 1991

[86] PCT No.: PCT/AU91/00347

§ 371 Date: Apr. 12, 1993

§ 102(e) Date: Apr. 12, 1993

[87] PCT Pub. No.: WO92/02624

PCT Pub. Date: Feb. 20, 1992

[30] Foreign Application Priority Data

Aug. 10, 1990 [AU] Australia .................. 1679/90

[51] Int. Cl.⁶ .................. G01N 33/569; G01N 33/53
[52] U.S. Cl. .................. 435/7.22; 435/7.92; 530/324; 530/822
[58] Field of Search .................. 435/7.22, 7.92, 435/6; 530/324, 810, 820, 822; 424/88, 93 R

[56] References Cited

U.S. PATENT DOCUMENTS 5,215,917  6/1993  De Araujo et al. .................. 435/252.33

FOREIGN PATENT DOCUMENTS

89/08700  9/1989  WIPO .................. 536/23.7

OTHER PUBLICATIONS

Johnson and Illana, "Cloning of *Toxoplasma gondii* gene fragments encoding diagnostic antigens", Gene, 99:127–132, (1991).

Tenter et al, "Recognition of recombinant *Toxoplasma gondii* antigens by human sera in an ELISA", Parasitol. Res., 77:197–203 (1991).

Prince et al, "Cloning of cDNAs encoding a 28 kilodalton antigen of *Toxoplasma gondii*", Mol. Biochem. Parasitol., 34:3–14 (1989).

Handman et al, "Detection and Characterization of Membrane Antigens of *Toxoplasma gondii*", J. Immunol., 124(6):2578–2583 (Jun. 1980).

Johnson et al, "Cloning, expression and nucleotide sequence of the gene fragment encoding an antigenic portion of the nucleotide triphosphate hydrolase of *Toxoplasma gondii*", Gene, 85:215–220, (1989).

*Primary Examiner*—Toni R. Scheiner
*Attorney, Agent, or Firm*—Birch, Stewart, Kolasch & Birch, LLP

[57] ABSTRACT

A synthetic or recombinant polypeptide displaying the antigenicity of all or an antigenic fragment of the H4 or H11 polypeptides of *Toxoplasma gondii*, and recombinant DNA molecules, vectors and host cells for the expression thereof. Use of the polypeptide in vaccine compositions and in diagnostic immunoassays is also disclosed.

12 Claims, 15 Drawing Sheets

```
Glu Phe Gln Glu Ile Lys Glu Gly Val Glu Glu His Lys His Glu Asp
GAA TTC CAA GAG GAA ATC AAA GAA GGG GTG GAG GAA CAC AAG CAT GAA GAC    51

Asp Pro Glu Met Thr Arg Leu Met Val Thr Glu Lys Gln Glu Ser Lys Asn
GAT CCT GAG ATG ACG CGG CTC ATG GTG ACC GAG AAG CAG GAG AGC AAA AAT   102

Phe Ser Lys Met Ala Lys Ser Gln Ser Phe Ser Thr Arg Ile Glu Glu Leu
TTC AGC AAG ATG GCG AAA TCC CAG AGT TTT AGC ACG CGA ATC GAA GAG CTC   153

Gly Gly Ser Ile Ser Phe Leu Thr Glu Thr Gly Val Thr Met Ile Glu Leu
GGG GGA TCC ATT TCG TTT CTA ACT GAA ACG GGG GTC ACA ATG ATC GAG TTG   204

Pro Lys Thr Ala Ser Glu His Asp Met Asp Gln Leu Leu His Asp Ile Leu
CCC AAA ACT GCT AGT GAA CAT GAC ATG GAC CAA CTA CTC CAC GAT ATT CTC   255

Ala Ala Val Glu Ser Leu Gly Ser Thr Pro Arg
GCC GTG GAG TCG GAG TTG GGC TCG ACT CCG AGG TGA AACTCGCATAGATGCACGA   310

CCCAGTCGATTTGCGAGTTATCGCGGACCGTGACTAGCAGCAGAGCTTTGTCAGCACGTATTTGTT   377
CTTGTGGCTAATATTAGCAACATGCCGATGGTTGTGGCATTCGGTATGCGATGTGAATAGTGCA    444
GTTTATGTTCACGAAAGAGTCGTTGGAGAGTCGGCAGAATGAGGCGACGGTTGTAGGC           511
CAGTTTGATTTTGTGTATTAGTGGTACTAGCAGAACATGCAAGGTGATGCGCTTGCATGGCTGAG   578
GATTCTCTTGGAGCTTTTTGCTCAGCATCAGAAGCGCGAACAAAGAATGTCCCTTTAAAGTGGGTGAC 645
AACCGCTGGAAAAAAAAAAAAAAAAAAGGAATTC                                   682
```

*Fig. 1A*

```
Glu Phe Pro Ala Lys Ala Val Lys Gly Phe Gly Gly Thr Arg Thr Ser Thr
GAA TTC CCC GCA AAG GCT GTC AAG GGA TTT GGT GGC ACC CGC ACT TCC ACG    51

Ala Pro Ala Glu Ala Gly Lys Thr Glu Leu Asp Asp Gly Tyr Arg Pro Pro
GCG CCT GCT GAG GCT GGA AAA ACG GAG TTG GAC GAC GGA TAT CGC CCG CCC   102

Pro Phe Asn Pro Arg Pro Ser Pro Tyr Ala Glu Leu Leu Lys Asp Leu Glu
CCA TTC AAC CCG CGA CCC TCA CCC TAC GCC GAG TTA TTG AAG GAT TTG GAA   153

Arg Met Arg Lys Glu
AGA ATG CGC AAA GAG TGA CCGTGCTGGGAAGCGAGTTCGAATTC                    197
```

*Fig.1B*

ABSORBANCE AT 405nm

RECIPROCAL OF SERUM DILUTION

MICE GROUPS

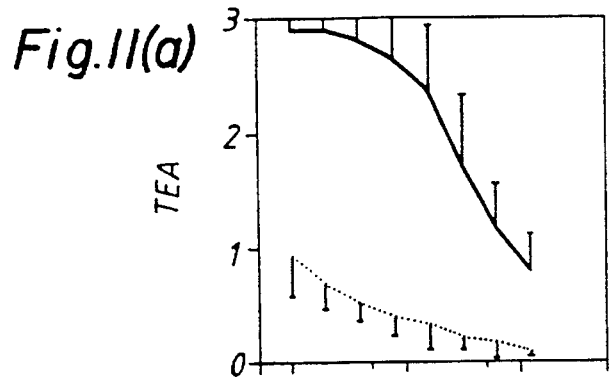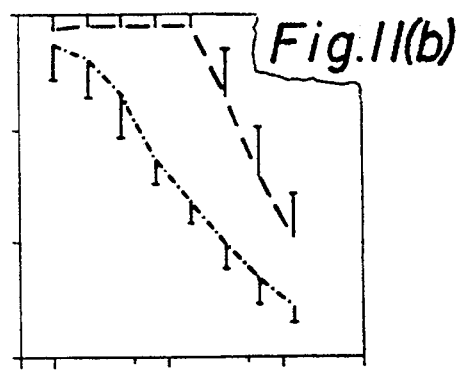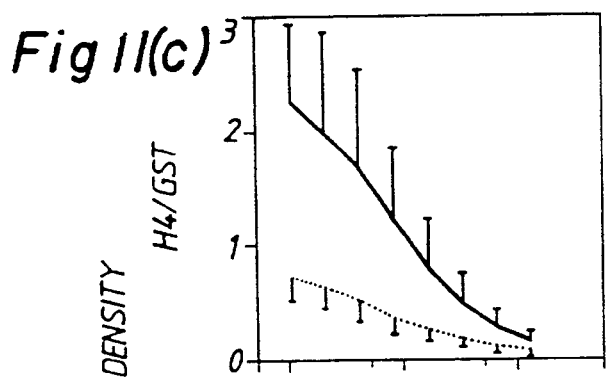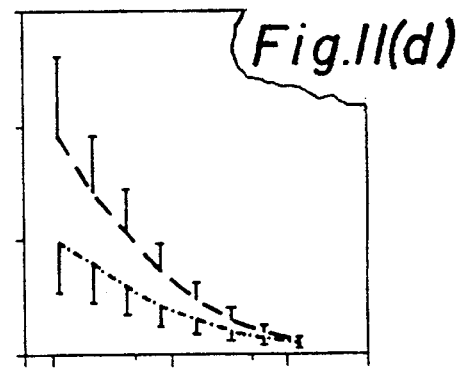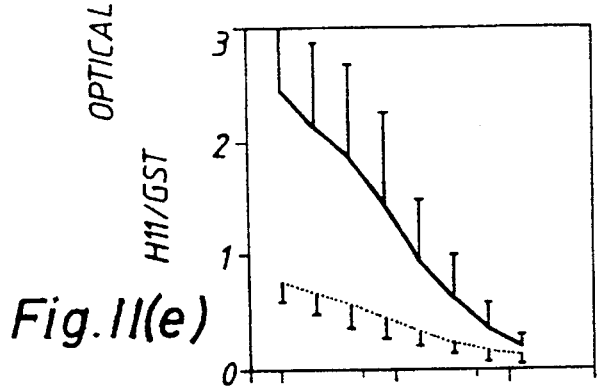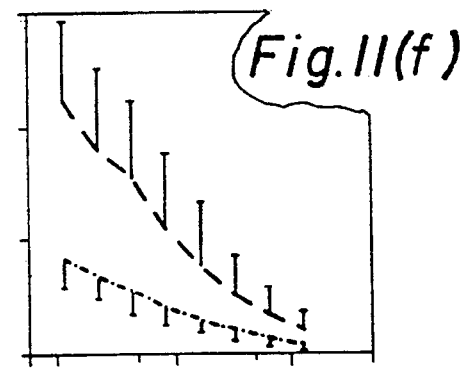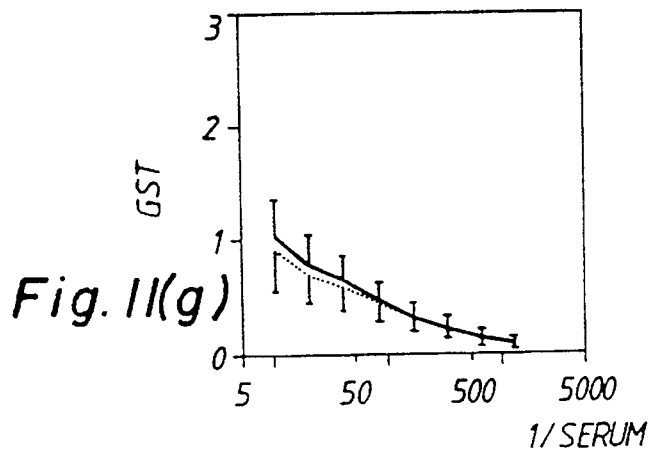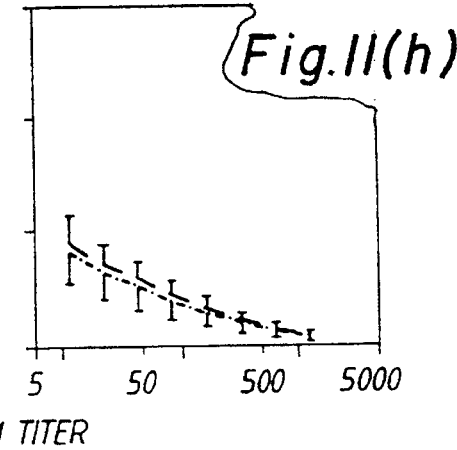

12.(c)

CLONING AND EXPRESSION OF TOXOPLASMA ANTIGENS AND USE OF RECOMBINANT ANTIGENS

This invention relates to the cloning and sequencing of two *Toxoplasma gondii* gene fragments, the encoded polypeptides of which can be used as diagnostic antigens, for example in an enzyme-linked immunosorbent assay (ELISA), or as active components in a vaccine against Toxoplasma. The invention also extends to the production of recombinant polypeptides by expression of these gene fragments in a host cell, and to the use of the expressed recombinant polypeptides as diagnostic antigens or as vaccine components.

*T.gondii* is an obligate intracellular protozoan of the order Coccidia. Humans usually acquire infection by ingesting either infectious oocysts through contact with cats or cat faeces, or by eating meat that contains tissue cysts (Dubey & Beattie, 1988). Once infected the host harbours the parasite for life. In a chronically infected individual who subsequently develops an immunodeficiency, caused by either drugs or by an underlying disease, the infection can reactivate and cause morbidity and mortality. The parasite can also be pathogenic if first acquired during pregnancy and may cause abortion or congenital infections.

Diagnosis of *T.gondii* infections is usually based on serological demonstration of IgG or IgM antibodies. For such a test, *T.gondii* antigens are required, but since the parasite is obligately intracellular, these antigen preparations are contaminated with host cells. This occurs regardless of whether the parasites are grown in tissue culture or in the peritoneal cavities of mice (Abbas, 1967). In addition, parasites have to be cultured which may be hazardous for workers, and the growth of the parasite in mice or tissue culture is expensive. The production of recombinant fusion proteins in bacterial or yeast hosts overcomes these problems and allows a standardized and reproducible assay to be performed.

Experimental work leading to the present invention has included the cloning and sequencing of two gene fragments that encode polypeptides which react in the ELISA for the serological diagnosis of *T.gondii* antibodies in sera from naturally infected humans, sheep and cats, and in experimentally infected mice. The production of recombinant antigens in bacterial or yeast cells offers a potential for the development of highly standardized diagnostic tests and well-defined, reproducible, and inexpensive antigens.

In an attempt to clone *T.gondii* genes which encode polypeptides likely to be important diagnostically, two different strategies have been followed. The first was to clone genes for antigens that constituted a large part of the tachyzoites, the actively dividing stage of the parasite. To that end, a gene fragment encoding an antigenic portion of the nucleoside triphosphate hydrolase of *T.gondii* has been cloned and sequenced (Johnson et.al., 1989). However, antibodies to this antigen have since been found to be present in only a low percentage of patients with chronic toxoplasmosis (Tenter and Johnson, 1990). The second strategy was to screen a cDNA library with several different types of antibody to *T.gondii*, and to test the antigens commonly identified for their usefulness in a diagnostic ELISA for toxoplasmosis. Using this second strategy, the present inventors have now identified fragments of two genes termed H4 and H11, which encode polypeptides that can be used as antigens in the ELISA to measure antibodies to *T.gondii* in human sera and murine sera, and these gene fragments have been expressed as fusion proteins in host bacteria. Such fusion proteins have the potential to replace the requirement for *T.gondii* to be grown in tissue culture or the peritoneal cavities of mice (Abbas, 1967) to prepare diagnostic ELISA antigen.

According to one aspect of the present invention, there is provided a recombinant DNA molecule comprising a nucleotide sequence which codes for all or an antigenic portion of the H4 or H11 polypeptides of *T.gondii*. Such a recombinant DNA molecule is capable of being expressed as a polypeptide displaying the antigenicity of all or an antigenic fragment of the H4 or H11 polypeptides of *T.gondii*.

By way of exemplification of this aspect of the invention, the DNA molecule may comprise a nucleotide sequence which corresponds to all or a portion of a base sequence substantially as shown in FIG. 1A or FIG. 1B, or degenerate variants thereof. As described in detail herein, the particular sequences shown in FIG. 1A and FIG. 1B have been identified as corresponding to the H4 and H11 gene fragments of *T.gondii*, and are capable of being expressed as polypeptides which have the predicted amino acid sequences as shown in FIG. 1A and FIG. 1B.

The H4 and H11 gene fragments are 682 bp and 197 bp long, respectively, and both are single copy genes. The mRNA of the H4 gene and H11 gene are 1,300 and 1,900 nucleotides in size, respectively. The predicted translation products of the H4 and H11 gene fragments are very hydrophilic, and are therefore likely to be exposed on the surface of their respective native polypeptides, which are 25 kDa and 41 kDa in size.

It will be appreciated that the nucleotide sequence of this aspect of the invention may be obtained from natural, synthetic or semi-synthetic sources; furthermore, this nucleotide sequence may be a naturally-occurring sequence, or it may be related by mutation, including single or multiple base substitutions, deletions, insertions and inversions, to such a naturally-occurring sequence, provided always that the DNA molecule comprising such a sequence is capable of being expressed as a polypeptide displaying the antigenicity of the H4 or H11 polypeptides of *T.gondii*.

The nucleotide sequence may have expression control sequences positioned adjacent to it, such control sequences being derived either from *T.gondii* nucleic acid or from a heterologous source.

This invention also provides a recombinant DNA molecule comprising an expression control sequence having promoter sequences and initiator sequences as herein defined, and a nucleotide sequence which codes for a polypeptide having the antigenicity of all or an antigenic fragment of the H4 or H11 polypeptides of *T.gondii*, the nucleotide sequence being located 3' to the promoter and initiator sequences.

In yet another aspect, the invention provides a recombinant DNA cloning vehicle capable of expressing all or an antigenic portion of the H4 or H11 polypeptides of *T.gondii*, comprising an expression control sequence having promoter sequences and initiator sequences, and a nucleotide sequence substantially coding for all or an antigenic portion of the H4 or H11 polypeptides of *T.gondii*, the nucleotide sequence being located 3' to the promoter and initiator sequences.

In a further aspect, there is provided a host cell containing a recombinant DNA cloning vehicle and/or a recombinant DNA molecule as described above.

In yet further aspects, there are provided fused polypeptides comprising polypeptide sequences displaying the antigenicity of the H4 or H11 polypeptides of *T.gondii*, and an additional polypeptide, for example a polypeptide coded for by the DNA of a cloning vehicle, fused thereto. Such a fused polypeptide can be produced by a host cell transformed or infected with a recombinant DNA cloning vehicle as described above, and it can be subsequently isolated from the host cell to provide the fused polypeptide substantially free of other host cell proteins.

The present invention also extends to synthetic polypeptides displaying the antigenicity of all or an antigenic portion of the H4 or H11 polypeptides of *T.gondii*. Preferably, at least a portion of a synthetic polypeptide of this aspect of the invention comprise an amino acid sequence as shown in FIG. 1A or FIG. 1B, or an antigenic fragment thereof.

As used herein, the term "synthetic" means that the polypeptides have been produced by chemical or biological means, such as by means of chemical synthesis or by recombinant DNA techniques leading to biological synthesis. Such polypeptides can, of course, be obtained by cleavage of a fused polypeptide as described above and separation of the desired polypeptide from the additional polypeptide coded for by the DNA of the cloning vehicle by methods well known in the art. Alternatively, once the amino acid sequence of the desired polypeptide has been established, for example, by determination of the nucleotide sequence coding for the desired polypeptide, the polypeptide may be produced synthetically, for example by the well-known Merrifield solid-phase synthesis procedure.

As used herein, the terms listed below have the following meanings:

Nucleotide: a unit of DNA or RNA comprising a sugar moiety (penrose), a phosphate and a nitrogenous heterocyclic base. The base is joined to the sugar moiety via the glycosidic carbon (1' carbon of the penrose) and the base characterises the nucleotide. The four DNA bases are adenine (A), guanine (G), cytosine (C) and thymine (T). The four RNA bases are A, G, C and uracil (U).

Recombinant DNA: a hybrid double stranded DNA sequence comprising at least two double stranded DNA nucleotide sequences, the first sequence not being found together in nature with the second sequence.

Cloning Vehicle: non-chromosomal double stranded DNA capable of replicating when placed within a unicellular micro-organism.

Bacteriophage: a cloning vehicle derived from viruses or bacteria which may infect certain strains of bacteria.

Plasmid: a cloning vehicle derived from viruses or bacteria.

Structural Gene: a sequence of DNA nucleotides which codes for a sequence of amino acids characteristic of a specific polypeptide.

Promoter Sequences: sequences of DNA nucleotides which control the initiation, rate or magnitude of transcription.

Initiator Sequences: sequences of DNA nucleotides which control the initiation of transcription.

Transcription: the process whereby RNA polymerase is caused to move along the DNA sequence forming messenger RNA.

Translation: the process of producing a polypeptide from messenger RNA.

Operon: a structural gene(s) coding for polypeptide expression which is preceded by initiator sequences.

Expression: the process involved in producing a polypeptide from a structural gene.

Lysogeny: the integration of bacteriophage nucleotide sequences into a bacterial genome.

A variety of techniques are available and well known for preparing the recombinant DNA molecule according to the invention, one of which comprises the steps of synthesising a single stranded DNA copy (cDNA) of the mRNA purified from an isolate of whole *T.gondii* using a reverse transcriptase enzyme, after which the cDNA is converted into a double strand (ds cDNA). An alternative method of preparing the double stranded cDNA is via chemical synthesis using techniques well known in the art.

Once the double stranded cDNA has been produced the next step is to insert it into a cloning vehicle, which may be for example a bacterial plasmid or bacteriophage. This may be achieved by first cleaving the DNA of the purified cloning vehicle, and the double stranded *T.gondii* cDNA can then be inserted between and linked to the open ends of the cloning vehicle by joining synthetic oligonucleotides to blunt ended ds cDNA and making the new termini cohesive by either exonuclease or endonuclease digestion, prior to ligation with appropriately linearized cloning vehicle. Alternatively, other techniques well known in the art may be used.

Once the double stranded *T.gondii* cDNA has been annealed with the DNA of the cloning vehicle, an appropriate host cell, such as a bacterium, is transformed, infected or lysogenized with the recombinant cloning vehicle, so as to permit the host cells to express the *T.gondii* ds cDNA, and thereby produce a polypeptide or polypeptides which may display *T.gondii* antigenicity.

There are several host cell-cloning vehicle combinations that could be used for the expression of *T.gondii* polypeptides, and suitable combinations are well known in the art (see, for example, Maniatis et.al. "Molecular Cloning, A Laboratory Manual", Cold Spring Harbor Laboratory).

Once recombinant DNA cloning vehicles and/or host cells expressing polypeptides displaying the antigenicity of the H4 or H11 polypeptides of *T.gondii* have been identified, the expressed polypeptides synthesised by the host cells, for example, as a fusion protein, can be isolated substantially free of contaminating host cell components by techniques well known to those skilled in the art.

Isolated polypeptides comprising, or containing in part, amino acid sequences corresponding to all or an antigenic portion of the H4 or H11 polypeptides of *T.gondii* may be used to raise polyclonal antisera by immunising rabbits, mice or other animals using well established procedures. Alternatively, such polypeptides may be used in the preparation of monoclonal antibodies by techniques well known in the art.

In addition, the polypeptides in accordance with this invention including fused polypeptides may be used as an active immunogen in the preparation of single or multivalent vaccines against *T.gondii* by methods well known in the art of vaccine manufacture. Such vaccines would be effective in stimulating antibodies in vaccinated animals, including humans, and thereby protecting against toxoplasmosis. Traditional vaccine formulations may comprise the antigenic polypeptides together with known adjuvants such as aluminium hydroxide, in association with a pharmaceutically acceptable carrier.

Alternatively, the polypeptides in accordance with the present invention including fused polypeptides may be used as antigen in a diagnostic immunoassay for detection of antibodies to *T.gondii* in a sample, for example, a serum sample from a human or other animal patient. Such immunoassays are well known in the art, and include assays such as radioimmunoassays (RIA) and enzyme-linked immunosorbent assays (ELISA).

Further details of the present invention, including the cloning and sequencing of the gene fragments termed H4 and H11, the production of recombinant H4 and H11 polypeptides by expression in *Escherichia coli* as glutathione-S-transferase (GST) fusion proteins, and the use of these H4/GST and H11/GST fusion proteins in the ELISA for serological diagnosis of *T.gondii* antibodies, are set out in the following Examples and the accompanying drawings.

EXAMPLE 1

Cloning and sequencing of H4 and H11 gene fragments

EXPERIMENTAL (a) Isolation of antigenic βGal fusion proteins.

A *T.gondii* cDNA library using RH strain tachyzoite poly(A)⁺RNA was constructed in λgt11 as described earlier (Johnson et.al., 1989). The library had a titre of $1.6 \times 10^9$ plaque forming units/ml and contained approximately 88% recombinant members with an average insert size of 1 kb. In order to identify the more commonly recognised βGal fusion proteins, the library was immunologically screened with 3 different types of sera: 50,000 members with rabbit antibody to denatured *T.gondii* antigens (RDen), identifying 15 positive clones; another 50,000 with a polyclonal immune mouse serum (PIMS), identifying 30 positive clones; and finally another 130,000 members with a serum from a patient (AL) naturally infected with *T.gondii*, identifying 27 positive clones. μGal positive fusion proteins were identified using an alkaline phosphatase conjugate screening procedure essentially as specified by the manufacturer (Promega Biotec, Madison, Wis.).

Positive clones recognised by one serum were then cross-checked by immunoscreening with the other 2 sera to test whether the recombinant antigens produced were recognised by all 3 sera. The results are set out in Table 1. The screening with the RDen serum was included because it has been found that screening λgt11 libraries with this type of antibody increases the efficiency of the screening (Timmins et.al., 1985). However, the 15 R clones were not recognised by either the PIMS or AL serum, and were consequently not further characterised. The lack of recognition of the H and M clones by the RDen serum, and the R clones by the PIMS and AL sera is perhaps not surprising, as antibodies to native proteins generally recognise conformational epitopes, (Rothbard, 1986) not those present in the denatured antigen used to immunise the rabbit. Interestingly however, the one M clone that was not recognised by the AL serum, and the one H clone, termed H39, that was not recognised by PIMS, were both identified by the RDen serum. Because the principal interest lies in the diagnosis of human toxoplasmosis, only the 27 H clones were purified by limiting dilution and rescreened, for further characterisation.

TABLE 1

Cross-screening of *Toxoplasma gondii* positive clones originally identified with one serum, against the other 2 sera.

| Type of clones | Serum | | |
|---|---|---|---|
| | RDen | PIMS | AL |
| ᵃR clones | 15 | — | — |
| ᵇM clones | 1 | 30 | 29 |
| ᶜH clones | 1 | 26 | 27 |

ᵃR clones denotes clones originally identified with the rabbit serum RDen; ᵇM clones denotes clones originally identified with the mouse serum PIMS; and ᶜH clones denotes clones originally identified with the human serum AL. RDen was prepared essentially as described by Timmins et.al. (1985). The RH strain tachyzoites used to immunize the rabbit were contaminated with about 5% murine peritoneal cells. PIMS was prepared as described elsewhere (Johnson et.al., 1983) except that the ovine II strain of *T.gondii* was used to chronically infect the mice.. This strain was isolated from an aborted fetal lamb in 1979 at Caveside, Tasmania, by Dr. B. L. Munday, Tasmanjan Department of Agriculture. Human serum used was from a patient (AL) suffering from acute lymphadenopathic toxoplasmosis who was bled 6 months after the onset of symptoms (Johnson et.al., 1987). Anti-*E.coli* antibodies were adsorbed from all three sera by incubating each serum with *E.coli* lysate several times (Helfman et.al., 1984).

(b) Nucleotide sequences.

Agarose gel electrophoresis of the 27 H clones revealed that the size of the DNA inserts were either about 200 bp, 670 bp or 1300 bp (not shown). To determine whether these inserts were identical EcoRI digested λgt11 preparations of the 27 H clones were probed with either a representative of the 200 bp inserts, termed H11 gene fragment, or a representative of the 670 bp inserts, termed H4 gene fragment. These results (not shown) suggested that 6 H clones were of the H11 type and 20 were of the H4 type. The clone termed H39 was unique and to date has not been characterised further.

FIGS. 1A and 1B show the nucleotide sequences of the H4 and H11 gene fragments (SEQ. ID NO. 1 and SEQ. ID NO. 3, respectively) and predicted amino acid (aa) sequences (A: H4 sequence (SEQ. ID NO. 2 and SEQ. ID NO. 4, respectively); B: H11 sequence). The *T.gondii* portions of the fusion proteins had predicted sizes of 10.9 kDa and 6.2 kDa for H4 and H11, respectively. The H4 and H11 gene fragments were subcloned into M13mp18 and sequenced in both directions by the dideoxy chain-termination method (Sanger et.al., 1977) using [³⁵S] dATP and the Sequenase™ kit (USB, Cleveland, Ohio).

Nucleotide sequencing revealed that the H4 fragment is 682 bp, of which only about 40% is translated as there is a stop codon at position 290 (FIG. 1A). The H11 gene fragment is 197 bp of which about 85% is translated as there is a stop codon at position 170 (FIG. 1B).

Both the H4 and H11 gene fragments and their corresponding predicted aa sequences were analysed by computer using the MacVector sequence analysis software, version 3.02 (MacVector Sequence Analysis Software: User's Manual, IBI, New Haven, Conn., 1989) on a Macintosh IIcx. Neither the H4 gene fragment, nor the H11 gene fragment sequence had significant homology with any gene sequence in the GenBank data base Release 61.0. There was also no significant homology to the 6 other *T.gondii* genes sequenced to date: P23 antigen (Cesbron-Delauw et.al., 1989); B1 antigen (Burg et.al., 1989); F3G3 antigen (Prince et.al., 1989); P30 antigen (Burg et.al., 1988); and α and β tubulin (Nagel and Boothroyd, 1988), or the NTPase gene fragment (Johnson et.al., 1989), or to each other.

The predicted aa sequences coded by either the H4 or H11 gene fragments had no significant homology with any protein in the NBRF PIR data base Release 19.0, or to each other.

(c) Molecular analysis of the H4 and H11 genes.

To determine the copy number of the H4 and H11 genes, *T.gondii* genomic DNA and known molar equivalents of plasmid containing either the H4 gene fragment or the H11 gene fragment were transferred to nylon membranes and hybridised with the respective purified gene fragment.

FIG. 2 shows quantitation of the H4 or H11 gene in *T.gondii* genomic DNA. 5 μg of *T.gondii* DNA (lane A) or the indicated molar equivalents of plasmid containing either the. H4 or H11 gene fragment, plus 5 μg of salmon sperm DNA, were digested with HindIII and resolved on a 1% agarose gel. The DNA samples were transferred to nylon membranes and probed with either [$^{32}$P]-nick translated H4 or H11 purified DNA inserts (Johnson et.al., 1986). The H4 and H11 gene fragments were purified from plasmid DNA by excision with EcoRI, separation in agarose and collection onto DEAE membranes.

The intensity of the autoradiographs obtained (FIGS. 2A and 2B) suggested that the H4 and H11 genes were both single copy.

Figure 3:
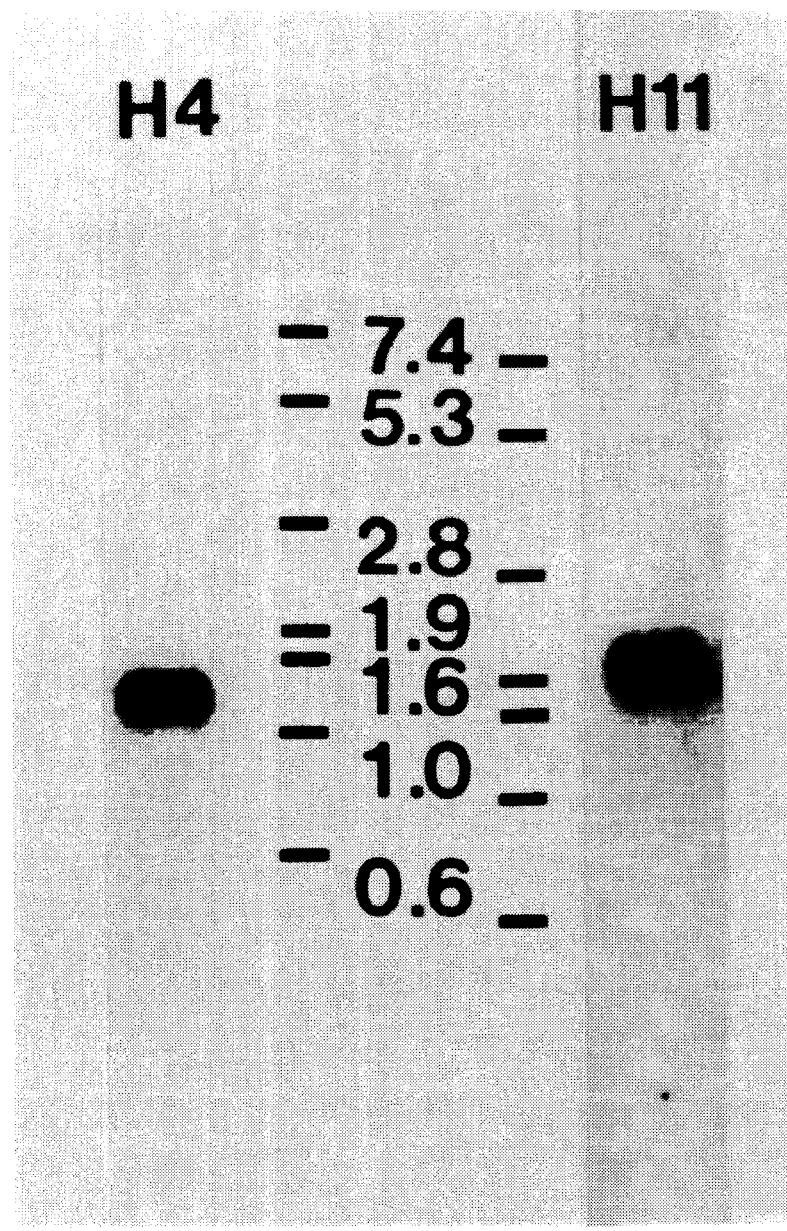

FIG. 3 shows Northern blot analysis of the H4 or H11 genes. 1 μg of *T.gondii* poly(A)$^+$RNA was electrophoresed on a 1.5% formaldehyde-agarose gel (Sambrook et.al., 1989) and transferred to a nylon membrane in duplicate. The membranes were probed with either [$^{32}$P]-nick translated H4 or H11 purified DNA inserts. Numbers in the middle indicate RNA molecular weight standards (kbp).

The mRNA for H4 and H11 were found to be 1,300 nucleotides (nt), and 1,900 nt, respectively (FIGS. 3A and 3B). The time taken to obtain a discernible hybridisation signal on the autoradiograph, compared with the time taken for a highly abundant mRNA to be detected (Johnson et.al., 1989), suggests that both the H4 mRNA and the H11 mRNA are not highly abundant.

(d) Western blot analysis.

To determine the sizes of the native polypeptides encoded by the H4 and H11 genes, immunoblots of *T.gondii* RH strain ELISA antigen (Johnson et.al., 1987) were reacted with the appropriate antibodies.

Figure 4:
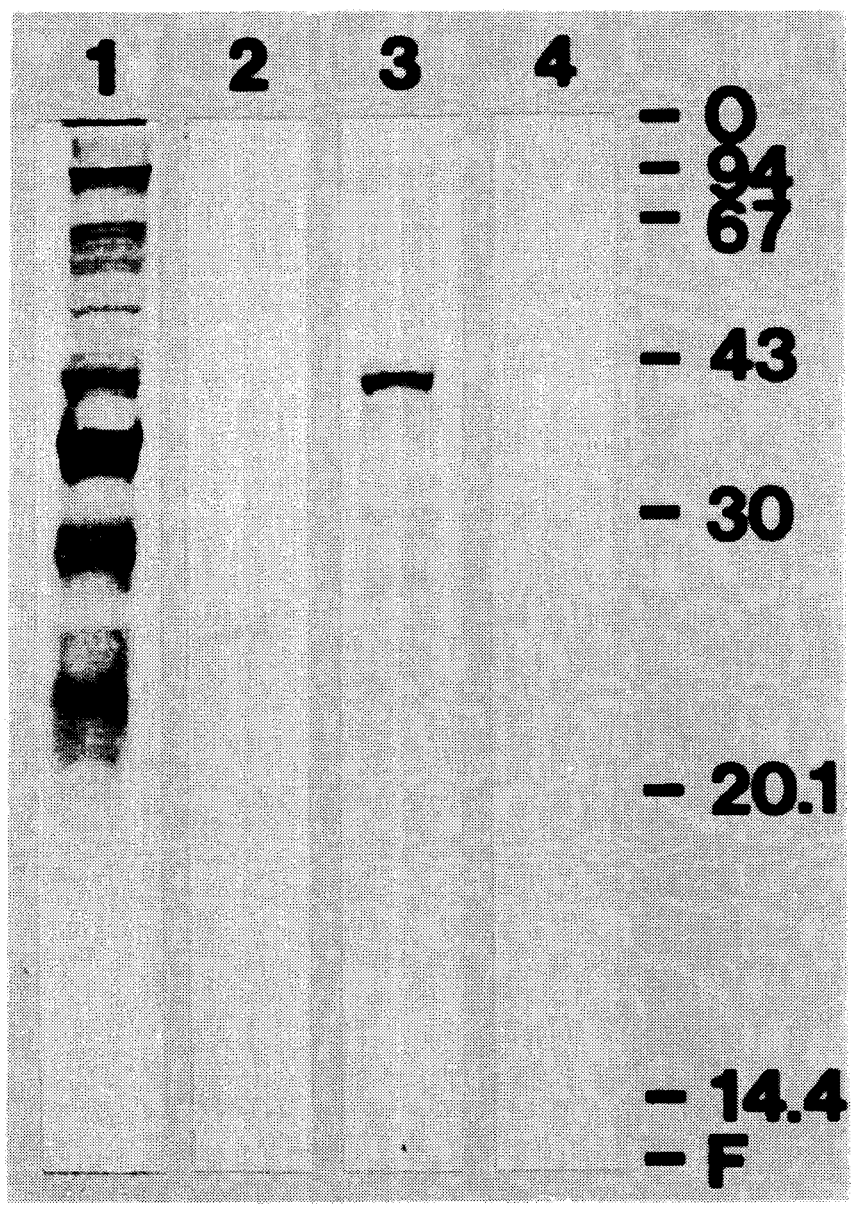
Figure 5A:
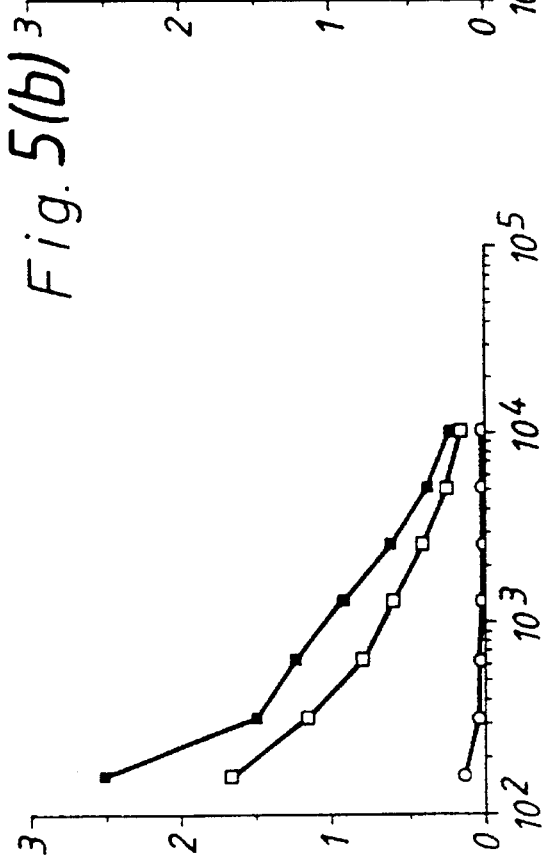
Figure 5B:
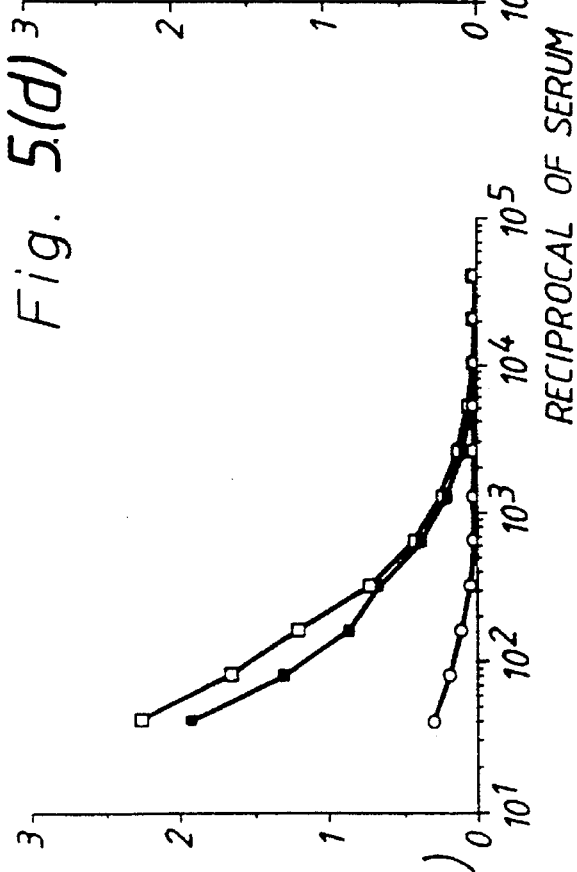
Figure 5C:
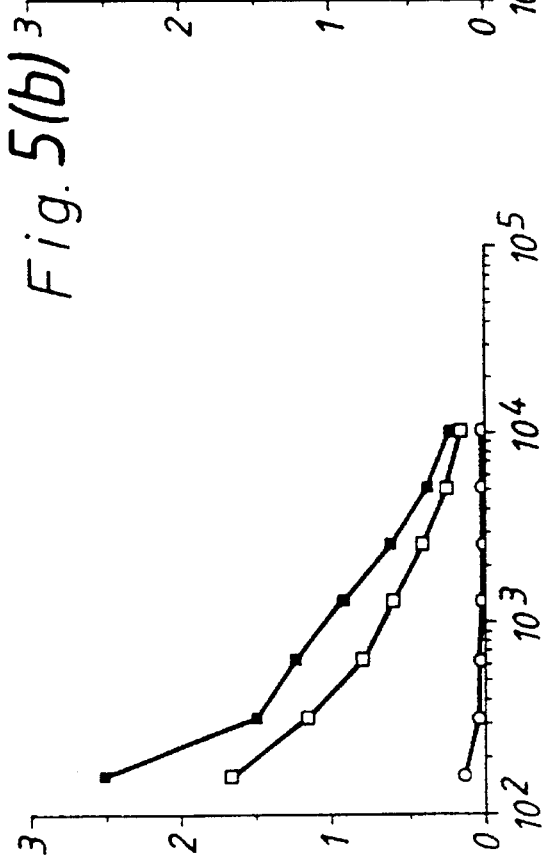
Figure 5D:
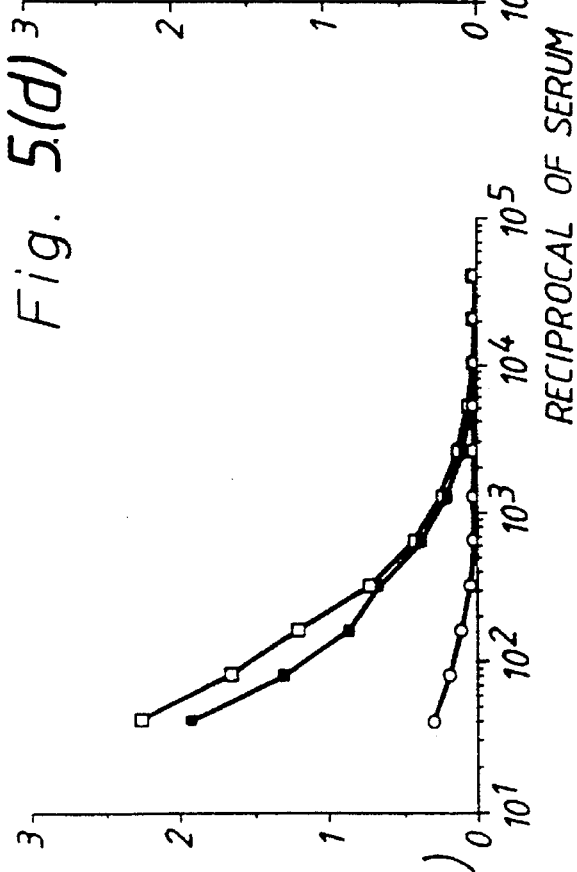

FIG. 4 shows Western blot analysis of the H4 or H11 gene products. H4 and H11 inserts were released from λgt11 by EcoRI digestion and subcloned into the EcoRI site of pGEX-1N. These clones were then expressed as GST fusion proteins in *E.coli*. Bacterial colonies were immunoscreened using a modified (Johnson et.al., 1989) procedure described previously (Helfman et.al., 1983) and the alkaline phosphatase conjugate system mentioned above. Fusion proteins were purified by absorption to glutathione-agarose beads as previously described (Smith and Johnson, 1988). Fusion proteins emulsified in Freund's Complete Adjuvant were injected into mice intradermally at several sites (Russo et.al., 1985). Mice were bled 4 weeks later. 300 μg samples of *T.gondii* RH strain ELISA antigen were resolved on 11% SDS-PAGE gels, transferred to nitrocellulose and reacted with 1:100 dilutions of: (lane 1) PIMS; (lane 2) Mouse anti-H4/GST; (lane 3) Mouse anti-H11/GST; and (lane 4) Mouse anti-GST antibody. Numbers on the right indicate molecular weight standards (kDa)—O denotes Origin, F denotes Front.

This showed that the H4 and H11 gene products were 25 kDa (lane 2) and 41 kDa (lane 3) respectively. Lane 4 shows that anti-GST antibody does not react with any *T.gondii* polypeptide which is consistent with the fact that the GST component of the fusion proteins does not play a part in the recognition of the native polypeptides.

EXAMPLE 2

Murine immune responses to recombinant *T.gondii* antigens

MATERIAL AND METHODS

Mice and Experimental Infections.

Inbred C57BL/6 and BALB/c mice were maintained in the laboratory under conventional conditions. Female mice were used for experiments when 10 to 14 weeks old.

Mice were infected with a pork isolate of *T.gondii* (Rothe et.al., 1985) which has been maintained by passages in laboratory mice. Animals were inoculated orally with either 20 tissue cysts from brains of chronically infected mice or 600 oocysts collected from a cyst infected cat (Johnson, 1988). Mice were bled prior to and at intervals following infection from the retro-orbital plexus.

In one experiment a number of different *T.gondii* isolates were used to infect mice. The isolates used were: FMC X, isolated from a human congenital infection at the Flinders Medical Centre in 1989; Ovine 2 (Rothe et.al., 1985); CHC/55, isolated from a cat in Western Australia in 1982 (Jackob-Hoff and Dunsmore, 1983); Pig, (G. Tiemann, dissertation, Tierarztliche Hochschule Hannover, West Germany, 1981). Mice chronically infected with the cyst stages of these isolates were bled and their sera collected for testing.

Preparation of antigens.

Tachyzoites of the RH strain of *T.gondii* were harvested from the peritoneal exudates of mice and disrupted by sonication (Johnson et.al., 1987). Recombinant *T.gondii* fusion proteins were expressed in *E.coli* transformed with the vector pGEX-1N (Smith & Johnson, 1988) containing gene fragments encoding either H4 or H11 (see Example 1). Production and purification of *T.gondii* fusion proteins and GST were performed as described by Smith and Johnson (1988).

Protein concentration was estimated by a Bradford dye-binding assay (Bradford, 1976).

Enzyme-linked immunosorbent assay.

The ELISA was performed essentially as described by Voller et.al. (1976), with some modifications. Flat-bottomed microtitre tray wells (Immuno Plate, Maxisorp F96, NUNC, Denmark) were coated with 100 μl of recombinant fusion protein (1 μg/ml) or *T.gondii* RH strain sonicate (5 μg/ml) diluted with 0.1M carbonate buffer (pH 9.8). A 30 min incubation, at 37° C., with 3% BSA in PBS+0.05% Tween-20 (PBS-T) was included to reduce non-specific binding. 100 μl of serum sample diluted in PBS-T was added to each well and plates incubated for 1 h at 37° C. The conjugate used was goat anti-mouse IgG labelled with alkaline phosphatase (Sigma). Plates were washed three times between each step with PBS-T. Binding was visualised with p-nitrophenyl phosphate (Sigma 104 phosphatase substrate tablets) in diethanolamine buffer (pH 9.8). Absorbance was read at 405 nm (EIA Autoreader EL 310, Bio-tek instruments) against a control well incubated with buffer alone.

Values shown are the mean for each group of mice, ±one standard error (SE) of the mean. Statistical evaluations were made by Student's t-test and differences at the 5% level were considered significant.

Delayed-type hypersensitivies (DTH).

Mice were clipped and immunised Intradermally (i.d.) with 100 μg antigen emulsified in Freund's complete adjuvant (CFA, Difco Laboratories). Five days later, animals were challenged in the test pinnae with 20 μg antigen in 10 μl PBS. Control ears received PBS alone. Ear thickness measurements were taken before challenge and at 24 h intervals thereafter. Ear swelling was calculated as 48 h measurement minus the baseline measurement taken at 0 hour.

In vitro cultures.

Spleen cells from control and infected mice were dissociated in RPM1 1640 medium (Flow Laboratories, Inc. U.S.A.). These cells were enriched for T cells by nylon wool purification (Julius, et.al., 1973). Cells were washed and suspended in RPM1 medium supplemented with $5×10^{-5}$M 2-mercaptoethanol, 2 mM glutamine, 10% foetal calf serum and penicillin/streptomycin (100 units/ml and 100 µg/ml). Spleen cells ($3×10^5$ per well) were cultured in 96 well flat bottom culture plates (Linbro, Flow Laboratories, Inc. U.S.A.) in the presence of various concentrations of the appropriate antigens, in triplicate. Macrophages ($5×10^3$ per well) from peritoneal washouts of uninfected mice were added, as antigen presenting cells. Positive (concanavalin A) and negative (unrelated foreign protein or culture medium alone) controls were included in all the assays. Cells were incubated for 72 h in a humidified, 37° C. 5% $CO_2$ atmosphere, pulsed with 0.4 µCi of [$^3$H] thymidine per well, and harvested 18 h later with a cell harvester. [$^3$H] thymidine incorporation was assessed by a standard liquid scintillation technique.

RESULTS

In the Figures:

FIGS. 5a, 5b, 5c and 5d show titration of sera in an ELISA with wells coated with: (a) *T.gondii* RH strain sonicate; (b) GST; (c) H4/GST; (d) H11/GST. Sera tested were from a pool of 10 uninfected C57BL/6 mice (O) or 18 weeks post infection with either cysts (□) or oocysts (■).

Figures 6A, 6B, 6C:
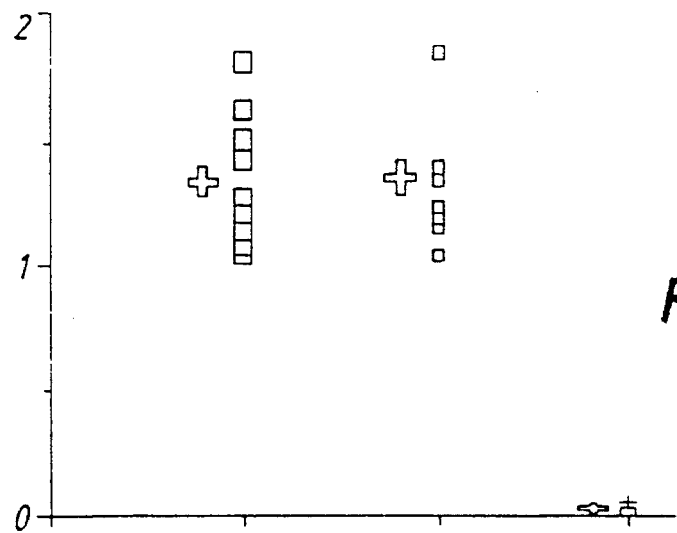

FIGS. 6a, 6b and 6c show absorbances in an ELISA with wells coated with: (a) *T.gondii* RH strain sonicate; (b) H4/GST; (c) H11/GST. Sera tested were from individual C57BL/6 mice which were either uninfected (+) or mice with an 18 week *T.gondii* cyst (□) or oocyst (■) infection. Serum dilutions used in each assay were: (a) 1/640; (b) 1/320; (c) 1/2560. Mean value±one SE is shown.

Figure 7A:
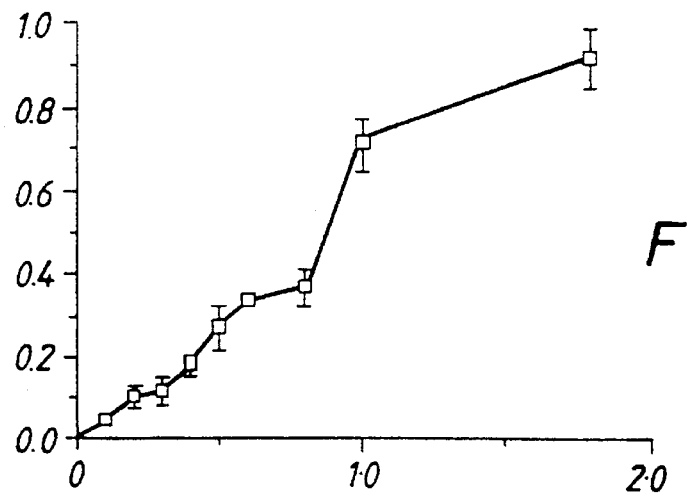
Figure 7B:
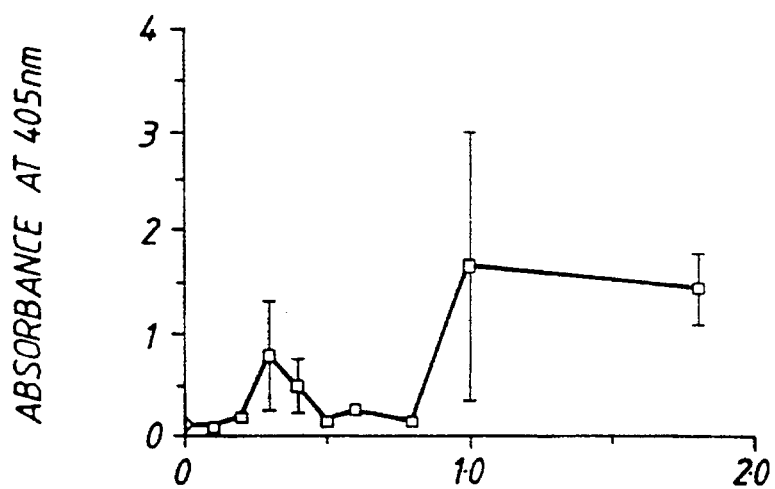
Figure 7C:
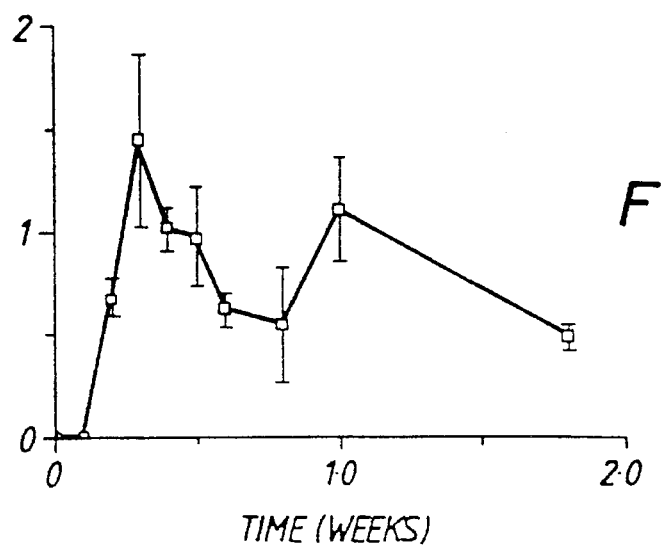

FIGS. 7a, 7b and 7c show results of an ELISA following infection on day 0 with *T.gondii* oocysts. Wells were coated with: (a) *T.gondii* RH strain sonicate; (b) H4/GST; (c) H11/GST. Serum dilutions were as for FIG. 6 apart from (c) which is 1/5120. The mean of 2 to 5 mice at each time point are shown, ±one SE where numbers of mice allowed.

Figure 8A:
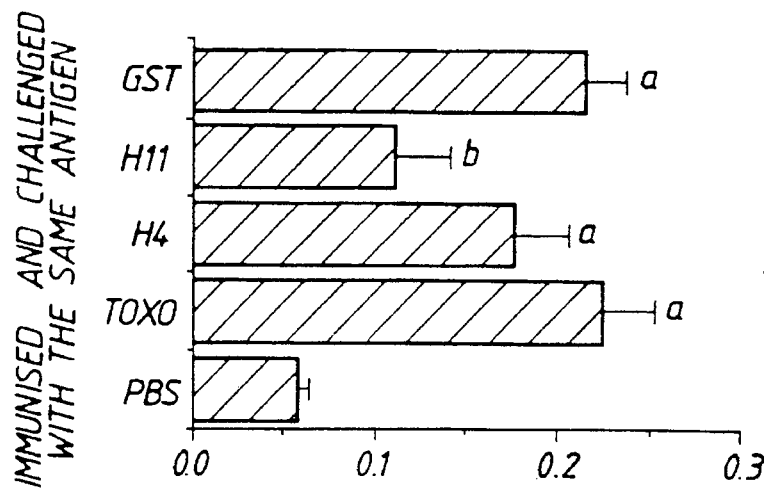
Figure 8B:
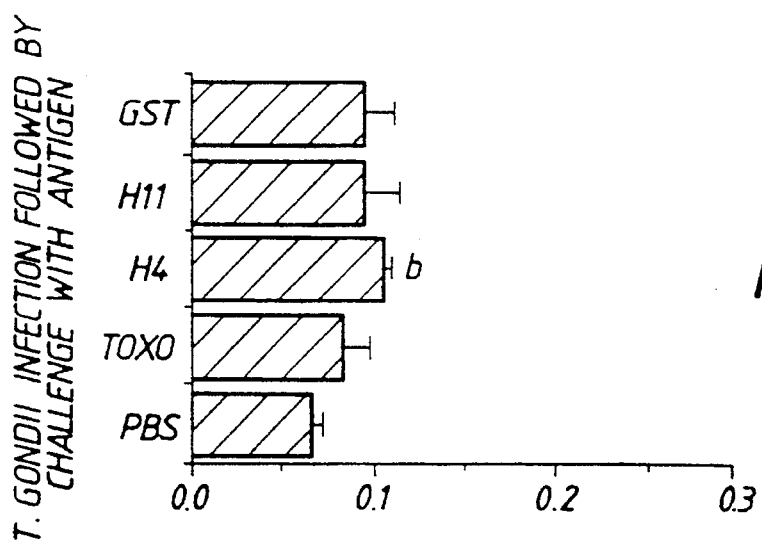
Figure 8C:
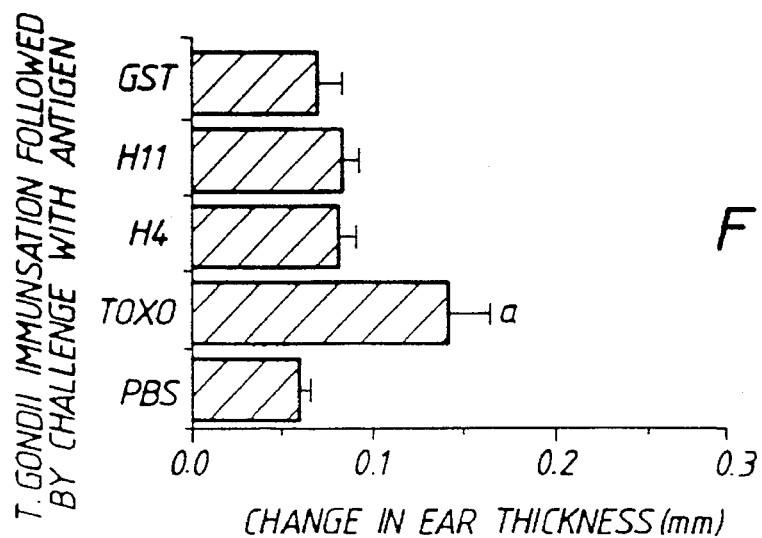

FIGS. 8a, 8b and 8c show groups of five BALB/c mice that were: (a) sensitised i.d. with antigen in CFA or PBS; (b) infected with 20 cysts of *T.gondii*; (c) immunised i.d. with *T.gondii* RH strain sonicate in CFA. Five days after immunisation or 21 days after infection, animals were challenged in the pinnae of the test ears with antigen and in control ears with sterile PBS. The value for PBS challenged ears is the mean for the 20 experimental mice. Increases in ear thickness at 48 h post challenge are shown, mean±one SE. A=p<0.01, b=p<0.05.

Figure 9:
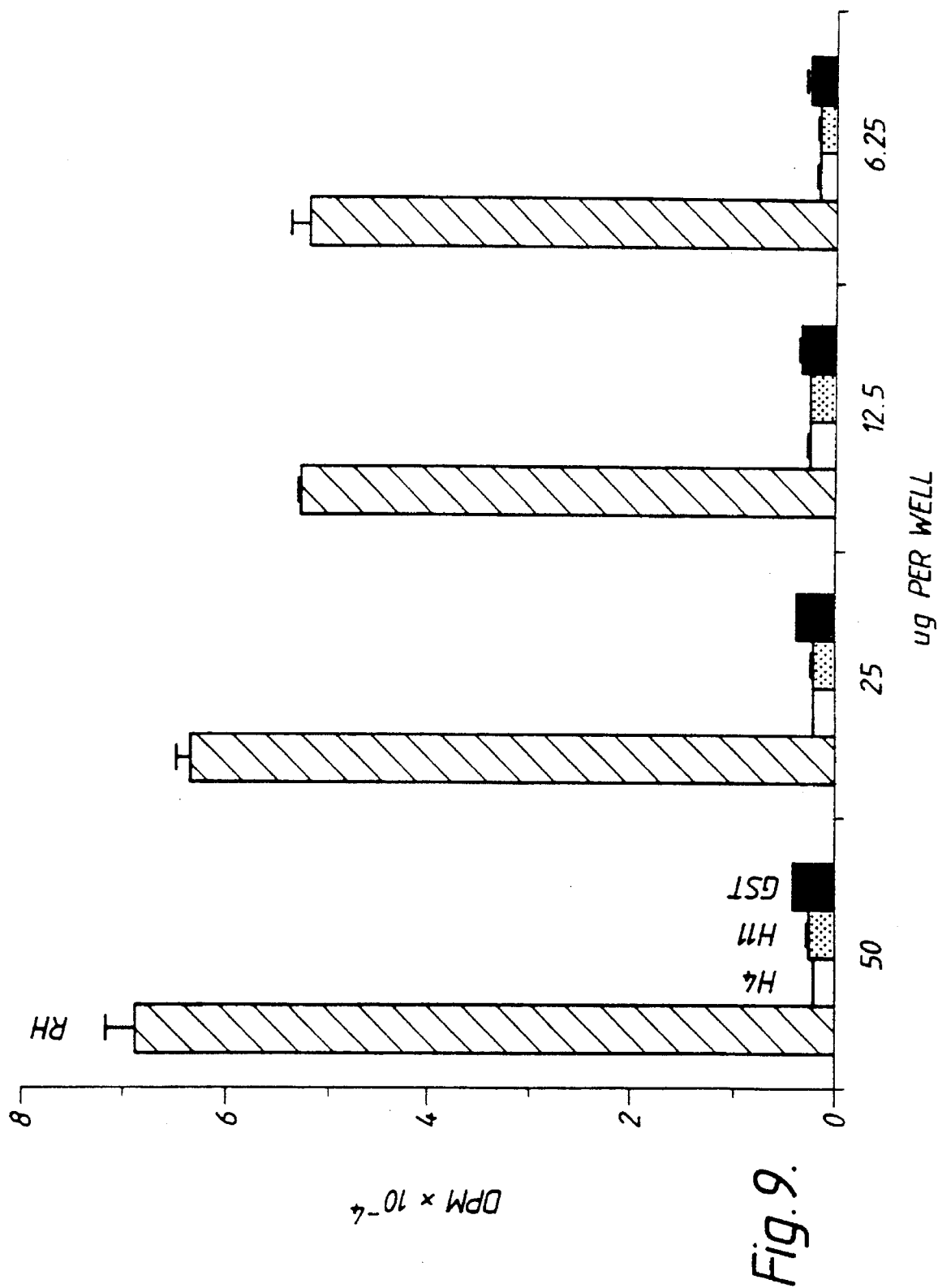
Figure 10A:
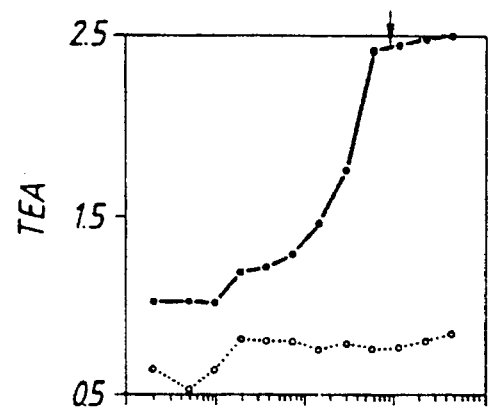
Figure 10B:
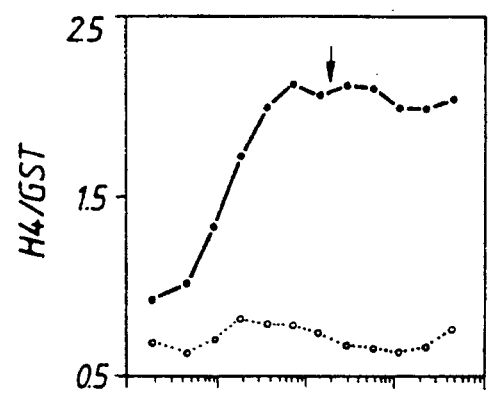
Figure 10C:
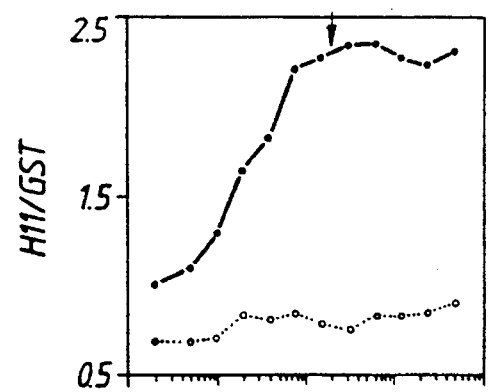
Figure 10D:
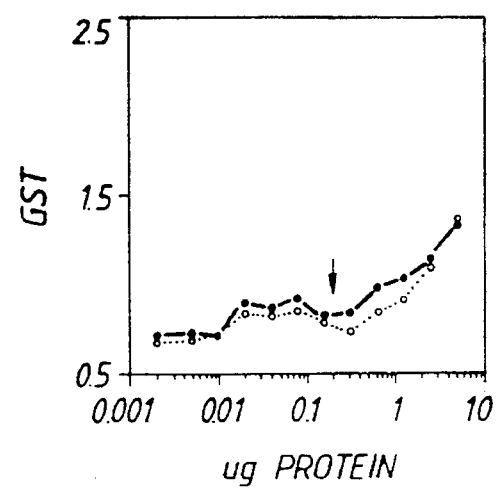

FIG. 9 shows lymphocyte proliferative responses of spleen cells from BALB/c mice chronically infected with *T.gondii* (dpm=disintegrations per minute). Antigens added to the cultures were: (▨), *T.gondii* RH strain sonicate; (□), H4/GST; ( ), H11/GST; (■), GST. Results are expressed as mean dpm±one SE. Background response, cells alone, was 1933±133.

Preliminary ELISA titrations.

The antigen preparation was titrated in a chequerboard fashion against a positive reference serum and against a negative reference serum. These samples were collected 18 weeks after infection with either *T.gondii* cyst or oocyst stages of the Pork isolate. Negative sera were from age matched uninfected animals. A pool was made of the 10 individual mice in each group. The optimum antigen concentration was determined at 1 µg/ml for the fusion proteins and 5 µg/ml for the *T.gondii* RH strain sonicate. The results of ELISA with a range of serum dilutions against these antigen concentrations are shown in FIG. 5.

Individual mouse antibody levels.

Once the optimum dilutions for the sera had been determined, the antibody response of individual mice was studied. From these results (FIG. 6) it can be seen that although there was some variation within the groups, all infected animals showed antibody titres significantly (p<0.05) above that found in uninfected animals for both H4/GST and H11/GST. However, of the two fusion proteins, H11/GST showed a clearer distinction between the means of the absorbances from infected and uninfected sera (p<0.01). Again antibodies from both oocyst and cyst infections recognised the fusion proteins.

Time course.

Once it was established that both cyst and oocyst infections produced antibodies against H4/GST and H11/GST, the antibody response to oocyst infection was studied over an 18 week period (FIG. 7). GST did not show any antibody binding (data not shown). A rise in anti-*T.gondii* titres over the first 10 weeks of infection was seen, after this time there was no further significant (p<0.05) increase in this antibody titre. The antibody response to H4/GST was delayed in comparison with the anti-*T.gondii* profile and did not appear until 18 weeks post infection. By contrast, the response against H11/GST developed early in the infection, by the second week (p<0.01) and peaked at 3 weeks after inoculation.

DTH.

Successful induction and elicitation of DTH responses was achieved with the H4/GST and H11/GST fusion proteins and sonicated *T.gondii* protein (FIG. 8a). The figure demonstrates that 48 h after antigenic challenge, significant (p<0.01) increases in ear thickness developed in mice immunised i.d. with antigen emulsified in CFA as compared with the ears sensitised with PBS in CFA. However, from these results, GST alone was able to stimulate a cellular response and it may be that it is this portion of the fusion protein that stimulates the cellular reaction.

In animals harbouring a 3 week old *T.gondii* infection, challenge with the different antigens produced an increase in ear thickness (p<0.05) only against the H4/GST protein when compared with the PBS control (FIG. 8b).

A reduction in responsiveness may be due to immunosuppression which is known to occur during the acute stage of *T.gondii* infection (Strickland et.al., 1975). To check this possibility, mice were sensitised with *T.gondii* RH strain sonicate and 5 days later challenged in the ear with the different proteins. In this experiment, only *T.gondii* RH strain sonicate stimulated a significant (p<0.01) cellular response and no change in ear thickness was noted for any of the other antigens (FIG. 8c).

Proliferation assays.

In vitro proliferation assays confirmed the in vivo assay results and demonstrated that only *T.gondii* RH strain sonicate was able to stimulate a significant (p<0.01) response in cells from infected animals (FIG. 9). The same result was also found for cells from mice immunised with *T.gondii* RH strain sonicate (data not shown).

Strain variation in antibody responses.

The fusion proteins produced were from a cDNA library made from *T.gondii* tachyzoites of the RH strain. In all the previous experiments, either cyst or oocyst infection of the Pork isolate was used. To determine whether the fusion proteins would be recognised by mice harbouring different T.gondii isolates, sera were collected from these mice and tested in an ELISA. GST and uninfected controls produced only low background values in all the assays (Table II). H11/GST was found to be recognised by anti-T.gondii antibodies in all four of the strains. Interestingly, however, H4/GST was recognised by only three of them. Antibodies in the sera of mice infected with the Ovine isolate did not bind to this fusion protein.

TABLE II

| Sera from mice infected with T. gondii isolate | ELISA coating antigen | | | |
|---|---|---|---|---|
| | T. gondii | H4/GST | H11/GST | GST |
| FMC X | 1.20 ± 0.05[a] | 1.75 ± 0.11[a] | 2.01 ± 0.01[a] | 0.05 ± 0.01 |
| Ovine | 0.68 ± 0.01[a] | 0.04 ± 0.00[b] | 1.09 ± 0.54[a] | 0.03 ± 0.00 |
| CHC/55 | 1.16 ± 0.14[a] | 0.98 ± 0.03[a] | 0.59 ± 0.02[a] | 0.08 ± 0.00 |
| Pig | 0.71 ± 0.02[a] | 0.14 ± 0.01[a] | 0.13 ± 0.01[a] | 0.09 ± 0.01 |
| Uninfected 1 | 0.08 ± 0.00[b] | 0.08 ± 0.01[b] | 0.08 ± 0.01[b] | 0.08 ± 0.01 |
| Uninfected 2 | 0.05 ± 0.00[b] | 0.02 ± 0.00[b] | 0.03 ± 0.00[b] | 0.04 ± 0.00 |

[a] $p < 0.05$ with respect to GST control
[b] not significant with respect to GST control.

All serum samples were assayed at a 1/1280 dilution apart from Pig sera, 1/320, and uninfected 2, which acted as a control for this sample. The values given are for individual mice run in triplicate wells and are representative of a number of animals tested. Uninfected control values were from a pool of sera from 10 mice. Mean±one SE is shown. Significances were determined by Student's t-test.

DISCUSSION

It is evident from the results presented here that two recombinant fusion proteins have been produced which are recognised by anti-T.gondii antibodies. In the preliminary ELISA titration, there is no indication that the GST portion of the fusion protein is being bound by the anti-T.gondii antibodies, as GST alone produces a low background value. Those wells coated with either T.gondii RH strain sonicate, H4/GST or H11/GST demonstrate clearly the binding of anti-T.gondii antibodies in the sera from infected animals as compared with uninfected mice. It is also evident from the results that both cyst and oocyst infected mice have antibodies that recognise the fusion proteins. These proteins have epitopes seen in experimental murine infections with either cysts or oocysts of the Pork isolate. However, it has been found that T.gondii possesses stage-specific antigens (Lunde & Jacobs, 1983) and strain specific antigens (Kasper et.al., 1984). Therefore, it is possible that fusion proteins identified from expression libraries and used as ELISA antigen candidates may not recognise T.gondii antibodies in all sera from humans with toxoplasmosis. It is rare to obtain sera from cases of human T.gondii infection definitively caused by either cysts or oocysts (Frenkel, 1990), and so we have used experimental infections in mice to test recognition of H4/GST and H11/GST.

The difference in detection of antibodies against H4/GST with the ovine isolate and the other T.gondii isolates illustrates such a specific antigen. A combination of a number of T.gondii fusion proteins may provide sensitivity with the benefits of using a known antigen and should allow the detection of most if not all different isolates of the parasite.

To investigate T cell responses to fusion proteins as compared with B cell reactions, we included here DTH and proliferation assays as well as the ELISA measurements. Interestingly, the T.gondii fusion proteins appeared to react in a test that should detect more conformational epitopes (ELISA) but not in tests that detected linear epitopes (DTH and proliferation assays). It is generally believed that T cell epitopes are linear due to the processing of the proteins by macrophages and B lymphocytes and/or proteolysis of the peptide chain epitopes (Chain et.al., 1988). Therefore, the GST part of the T.gondii fusion proteins may be initiating some secondary and tertiary folding of the protein required for antibody binding.

The time course results presented here show that although both H4 and H11 are antigenic in these infections, the H11/GST fusion protein is detected earlier by the circulating antibodies than the H4/GST fusion protein. Indeed, although antibodies to the T.gondii RH strain sonicate were detectable by this time, there would appear to be a quantitative difference between the H11 and T.gondii RH strain sonicate. In fact, it is possible that the use of H11 fusion protein in ELISA for human infection rather than sonicated RH strain T.gondii may result in a test that can give a positive result sooner in the infection.

EXAMPLE 3

Recognition of recombinant T.gondii antigens by human sera

MATERIALS AND METHODS

Preparation of antigens.

Tachyzoites of the RH strain of T.gondii were harvested from the peritoneal exudates of mice and disrupted by sonication as previously (Johnson et.al., 1987). This type of antigen preparation will be termed traditional ELISA antigen (TEA).

The gene fragments encoding H4/GST or H11/GST were subcloned from a λgt11 expression library into the plasmid pGEX-1N, and the two polypeptides were then expressed in Escherichia coli strain JM105 as GST fusion proteins and purified under non-denaturing conditions by adsorption to glutathione-agarose beads following a modification of the method of Smith and Johnson (1988) (see Example 1). GST was produced from cultures of E.coli containing pGEX-1N following the same procedure as for the recombinant T.gondii antigens. The protein concentration of the antigen preparations was determined by a commercial Bradford dye-binding assay (Bio-Rad Protein Assay; Bio-Rad Chemical Division, Richmond, Calif., U.S.A.).

Sera.

The 253 *T.gondii* positive and 151 negative sera used here were obtained from 404 patients who were investigated at the Flinders Medical Centre between 1985 and 1990 for a variety of symptoms or conditions in which toxoplasmosis may be important. All sera were examined at a dilution of 1/200 in a classical ELISA for parasite-specific IgG antibodies (Dahl and Johnson, 1984) and in an antibody class capture ELISA for parasite-specific IgM antibodies (Johnson et.al., 1985) on first presentation. Both of these tests use TEA. According to the reactions given in these two tests, the sera were placed into one of three groups: (1) sera that were negative in both tests were defined as being from patients that were not infected with *T.gondii*; (2) sera that were positive in both tests were defined as being from patients with acute toxoplasmosis; (3) sera that were negative for IgM antibodies, but positive for IgG antibodies were defined as being from patients with chronic toxoplasmosis.

In order to check the recombinant antigens for cross-reactivity with heterologous antibodies, sera from 18 patients infected with *Echinococcus granulosus*, 8 patients infected with *Entamoeba histolytica*, 26 patients infected with *Toxocara canis*, 3 patients infected with *Trichinella spiralis*, 27 patients infected with Epstein-Barr virus, and 12 patients with rheumatoid factor were included. All of these sera were negative for IgM and IgG antibodies to TEA.

Determination of optimum conditions of the assays.

For preliminary experiments, four serum pools were constructed from: (1) sera of 12 patients that were not infected with *T.gondii*; (2) sera of 12 patients with acute toxoplasmosis; (3) sera of 12 patients with chronic toxoplasmosis showing high IgG antibody levels to TEA; and (4) sera of 12 patients with chronic toxoplasmosis showing moderate IgG antibody levels to TEA. These serum pools were used as reference sera in chequerboard assays with serial dilutions of antigens, sera, and conjugate. The optimal concentrations of each of the four antigens, (TEA, H4/GST, H11/GST, and GST) and of the conjugate, were determined from the results given by these chequerboard assays. The conjugate used was goat anti-human IgG (H+L) conjugated to alkaline phosphatase (antibody concentration 0.6 mg/ml; Jackson Immunoresearch Laboratories, West Grove, Pa., U.S.A.) which reacts with heavy chains of human IgG and with light chains common to most human Ig.

In order to determine the optimal serum dilution for the screening of single human sera, the 48 sera that were used to construct the positive and negative reference sera were titrated from 1/10 to 1/1280. The serum dilution that rendered the highest difference in optical densities (O.D.) measured for positive and negative sera and for the recombinant *T.gondii* antigens and GST was chosen for the screening of all 253 *T.gondii* positive and 151 negative sera. The four reference sera were included as controls in all screening tests and were examined 8 times in the same test and once in 11 different tests to assess the reproducibility of the assays.

ELISA procedure.

ELISA plates (Immuno Plate Maxisorp F96; A/S NUNC, Roskilde, Denmark) were incubated (15 h, 4° C.) with 100 μl/well of the antigens (TEA, H4/GST, H11/GST or GST) diluted with coating buffer (0.015M carbonate 0.035M bicarbonate, pH 9.6) or of coating buffer alone and then washed (Titertek Microplate Washer 120; Flow Laboratories, Irvine, Scotland, UK) 5 times with 0.01M phosphate-buffered 0.15M saline (PBS), pH 7.4. The sensitised wells were post-coated with 100 μl of 3% w/v BSA (bovine albumin; Cohn fraction V powder; Sigma Chemical Company, St. Louis, Mo., U.S.A.) in PBS (1 h, 37° C.) and then washed 5 times with PBS containing 0.2% v/v Tween-20 (PBS-Tween). Each of the four different antigen-coated wells and a coating buffer control well were incubated (1 h, 37° C.) with 100 μl of each serum sample diluted with 1% BSA in PBS-Tween. The plates were washed as before and incubated with 100 μl/well of conjugate diluted with 1% BSA in PBS-Tween. The plates were then washed 5 times each with PBS-Tween and deionised water, and incubated (22° C.) with 80 μl/well of 0.1% p-nitrophenyl phosphate (Sigma 104 phosphatase substrate tablets; Sigma Chemical Company) in 10% w/w diethanolamine buffer containing 0.5 mM magnesium chloride, pH 9.8. The substrate reaction was stopped after 10 min by the addition of 50 μl of 2M sodium hydroxide. The O.D. values were measured at a wavelength of 405 nm (EIA Autoreader EL 310; Bio-Tek Instruments, Burlington, Vt., U.S.A.) against a control well that had not received serum or conjugate. In order to account for non-specific high background binding to the ELISA plate itself given by some human sera, the O.D. values measured in the screening tests for single sera were converted into indices using the following formula:

$$\text{Index} = \text{O.D.}_{(antigen\text{-}coated\ well)} - \text{O.D.}_{(coating\ buffer\ control\ well)}$$

Coefficients of variation (CV) were calculated from the arithmetic mean ($\bar{x}$) and standard deviation (SD) using the formula $CV = SD/100\bar{x}$. In order to calculate the correlation among the ELISA using the recombinant antigens and the ELISA using TEA, regression analyses were used which were done with a scientific graph software program (Sigma-Plot; Jandel Scientific, Corte Madera, Calif., U.S.A.).

RESULTS

In the figures:

FIGS. 10(*a*)–10(*d*) show determination of optimal antigen concentrations. Data are shown for: a 1/20 dilution of the reference serum from patients with acute toxoplasmosis (t); a 1/20 dilution of the reference serum from patients not infected with *T.gondii* (O); and a 1/500 dilution of conjugate. Arrows indicate the antigen concentrations chosen for the screening of single sera.

FIGS. 11(*a*)–(*h*) show determination of optimal serum dilution for the screening of single sera. Data shown are: (—) $\bar{x}$+SD for 12 sera from patients with acute toxoplasmosis; (- - -) $\bar{x}$+SD for 12 sera from patients with chronic toxoplasmosis showing high IgG antibody levels to TEA; (-.-.-.) $\bar{x}$−SD for 12 sera from patients with chronic toxoplasmosis showing moderate IgG antibody levels to TEA; and (.....) $\bar{x}$−SD for 12 sera from patients not infected with *T.gondii*. A serum dilution of 1/50 was chosen for the screening of single sera.

Figure 12:
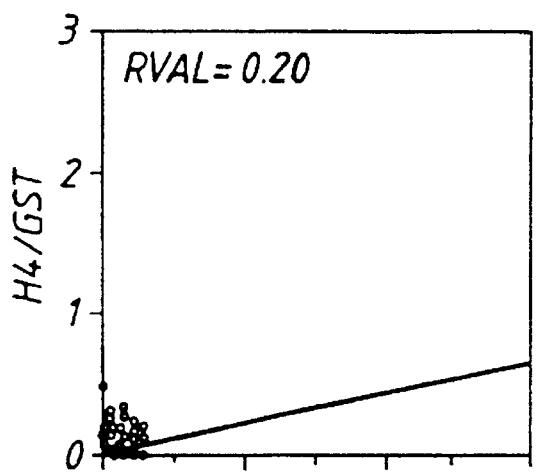
Figure 12:
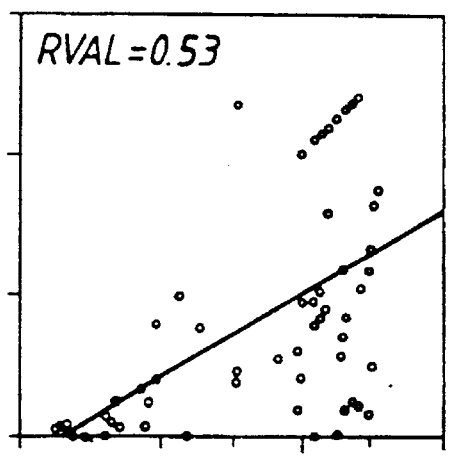
Figure 12C:
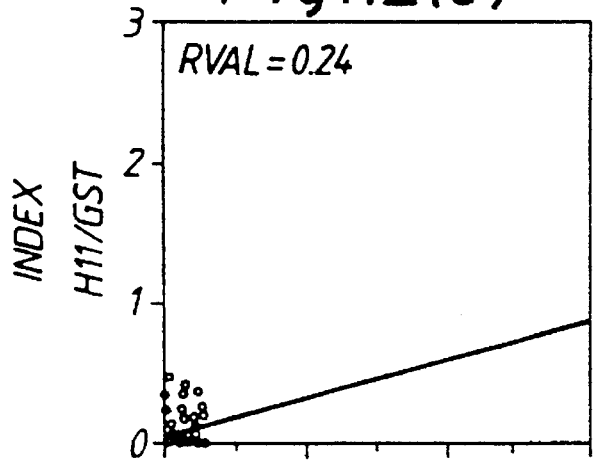
Figure 12D:
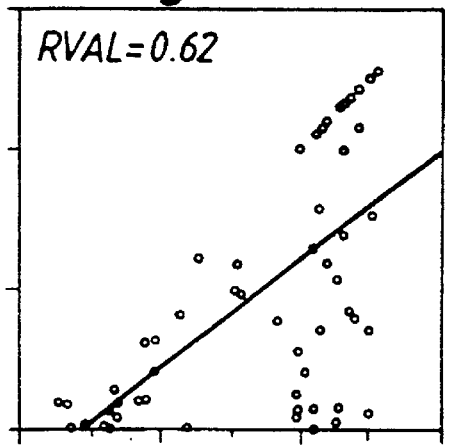
Figure 12E:
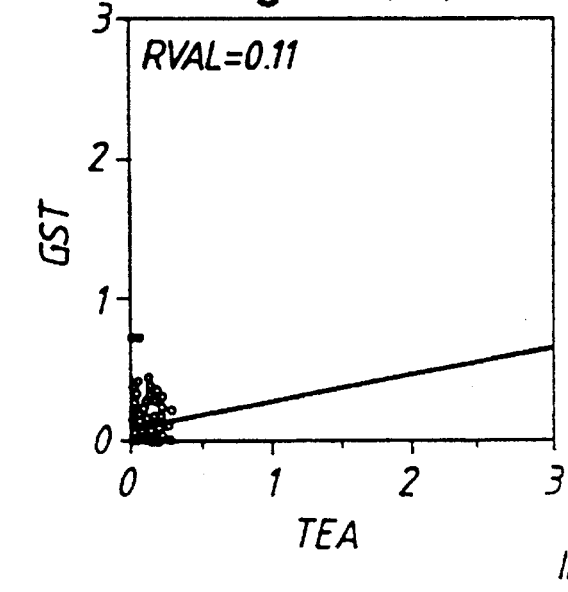
Figure 12F:
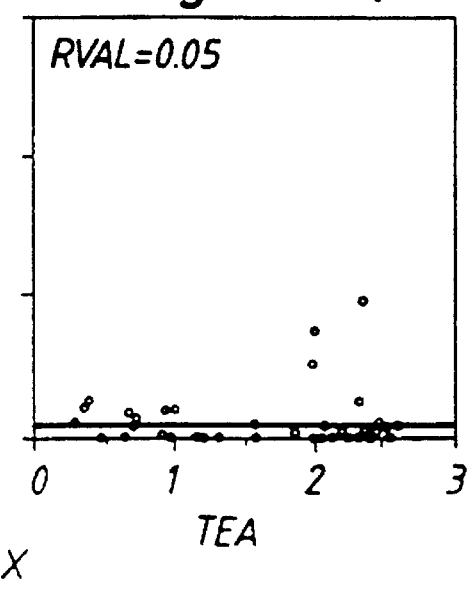
Figure 12G:
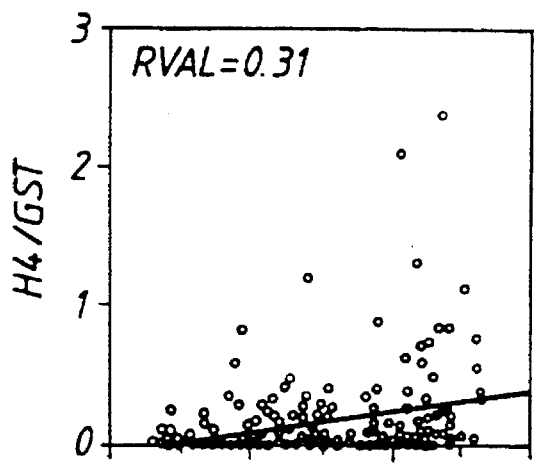
Figure 12H:
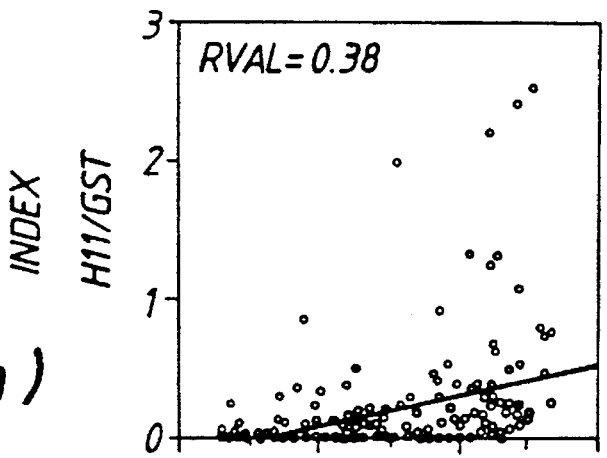
Figure 12I:
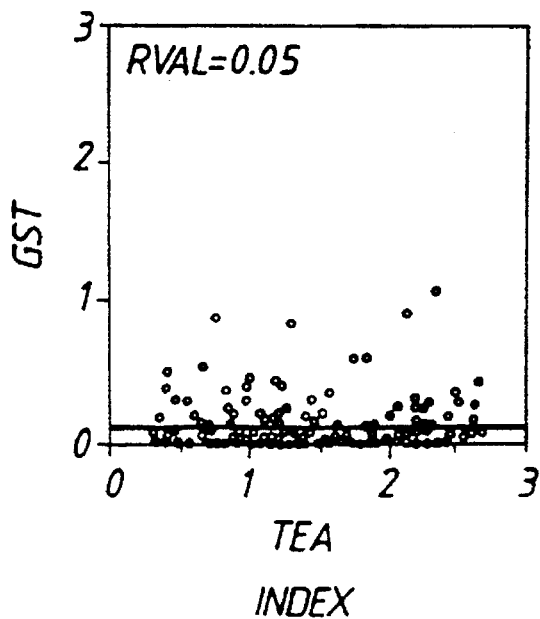

FIGS. 12(*a*)–12*i* show regression analyses for reactions with TEA and reactions with the recombinant antigens given by 404 single sera at a dilution of 1/50: (A) 151 sera from patients not infected with *T.gondii*; (B) 59 sera from patients with acute toxoplasmosis; (C) 194 sera from patients with chronic toxoplasmosis.

Figure 13A:
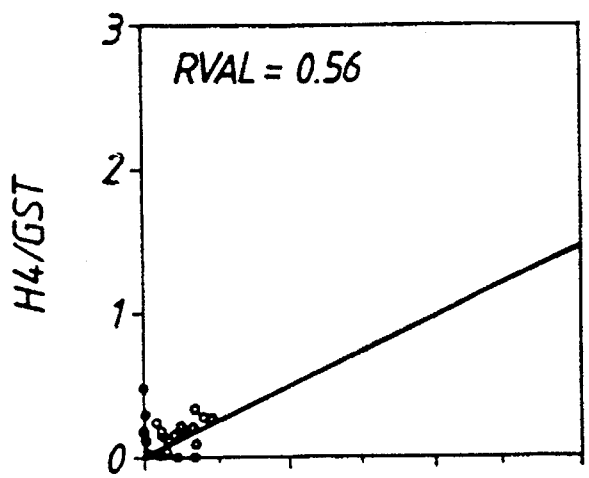
Figure 13B:
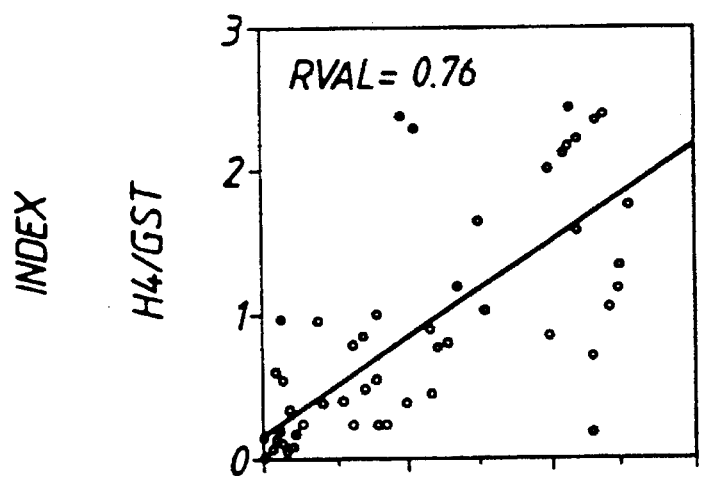
Figure 13C:
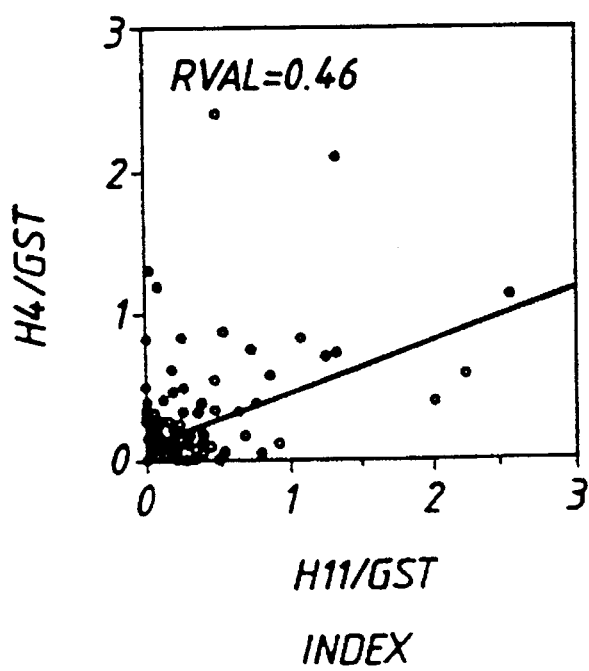

FIGS. 13*a*, 13*b* and 13*c* show regression analyses for reactions with H4/GST and reactions with H11/GST given by 404 single sera at a dilution of 1/50: (A) 151 sera from patients not infected with *T.gondii*; (B) 59 sera from patients with acute toxoplasmosis; (C) 194 sera from patients with chronic toxoplasmosis.

Conditions and reproducibility of the ELISA.

The chequerboard assays determined an optimal antigen concentration of 1 μg protein/well for TEA and of 0.2 μg protein/well for H4/GST and H11/GST (FIG. 10). GST was used at the same concentration as the recombinant *T.gondii* antigens. The optimal dilution of conjugate was 1/500 with all four antigens. The best discrimination between *T.gondii* positive and negative sera and between the recombinant *T.gondii* antigens and GST was observed at a serum dilution of 1/50 (FIG. 11). At this serum dilution, both assays using the recombinant *T.gondii* antigens showed a good reproducibility, (CV<12), both within the same test and among different tests.

Sensitivity and specificity of the ELISA.

A positive correlation was found between reactions with TEA and reactions with H4/GST or H11/GST for all groups of patients (FIG. 12). Correlation was high ($P \leq 0.001$) for sera from patients with acute or chronic toxoplasmosis and marginal ($P<0.04$) for sera from patients not infected with *T.gondii*. No significant correlation ($P \leq 0.33$) was observed between reactions with TEA and reactions with GST. Correlation was always high ($P<0.001$) between reactions with H4/GST and reactions with H11/GST (FIG. 13).

The sensitivity was considerably higher for sera from patients with acute toxoplasmosis than for sera from patients with chronic toxoplasmosis. In total, 68% of the sera from patients with acute toxoplasmosis recognised at least one of the recombinant *T.gondii* antigens. By contrast, only 3% of all 404 sera reacted positively with GST. None of the sera from patients with echinococcosis, entamoebosis, toxocarosis, trichinellosis, glandular fever, or rheumatoid arthritis, that were not infected with *T.gondii*, reacted positively with either H4/GST or H11/GST, but one of the 27 sera from patients with glandular fever reacted positively with GST.

DISCUSSION

The quality of ELISA depends on the specificity, affinity, and avidity of the antigens and antibodies involved. The recombinant *T.gondii* polypeptides used here were investigated for their suitability as diagnostic antigens for human toxoplasmosis because: (1) they originated from a cDNA library constructed from poly $(A)^+$ RNA of tachyzoites (Johnson et.al., 1989), which is the proliferative stage present during the acute phase of infection, (2) they were recognised by immunoscreening the cDNA library with polyclonal anti-*T. gondii* sera from experimentally infected mice as well as a naturally infected human patient with acute lymphadenopathic toxoplasmosis, (3) antisera produced against H4/GST or H11/GST recognised native polypeptides of about 25 kDa and 41 kDa, respectively, in Western blots of *T.gondii* tachyzoites, (4) both recombinant polypeptides were capable of detecting specific antibodies in the sera of mice infected experimentally with one of the two orally infectious stages, oocysts or cysts, of *T.gondii* (see Example 2).

The results presented here showed that both recombinant *T.gondii* polypeptides had a high specificity for antibodies to *T.gondii*. Neither H4/GST nor H11/GST reacted positively with any of the sera from humans that were not infected with *T.gondii*, including humans that suffered from other parasitic diseases, glandular fever, or rheumatoid arthritis.

EXAMPLE 4

Comparison of different ELISAs in diagnosis of acute toxoplasmosis

This Example compares three commercially available ELISAs for the diagnosis of acute toxoplasmosis with a laboratory produced antibody-class capture (Naot et.al.; Johnson et.al., 1985) ELISA (FMC-ELISA), and an ELISA using recombinant *T.gondii* fusion polypeptides as antigen (REC-ELISA).

MATERIALS AND METHODS

ELISAs.

ELISAs that were included in this Example were manufactured by: Abbotts Laboratories Diagnostics Division, Abbott Park, Ill. 60064, U.S.A. (batch number 47887M100 expiry date 19 Jun. 1991); Mercia Diagnostics Limited, Broadford Park, Shalford, Surrey GU4 832, UK (batch number 42 expiry 11 Jan. 1991); and Sorin Biomedical Diagnostic Division 13040 Saluggia, Vercelli, Italy (batch number 2350690A expiry date 3 Oct. 1991).

In the study reported here, the REC-ELISA antigen was an equal mixture of H4/GST and H11/GST, not separate H4/GST or H11/GST as used in the previous Example. Both the ABBOTT-ELISA and REC-ELISA are indirect type ELISAs, the FMC-ELISA and SORIN-ELISA are antibody capture type ELISAs with unlabelled antigen, and the MERCIA-ELISA is an antibody capture type ELISA with labelled antigen.

Serum panel. Sera were used from patients with a varying range of symptoms, and were divided into four groups: Group 1–38 sera from 27 patients known to have acute toxoplasmosis and *T.gondii*-specific IgM, as detected by the FMC-ELISA. Six samples were sequential bleeds from one patient, 12 sera were single samples from eight patients, and 12 sera were provided by an Austrian and a French laboratory. Group 2: 15 sera from 13 patients who had no previous history of exposure to *T.gondii* and were seronegative for both *T.gondii*-specific IgG and IgM as detected by the FMC-ELISA for IgM and a standard ELISA for IgG. Group 3: 15 sera from 15 patients who had no previous history of exposure to *T.gondii* and were seronegative for both *T.gondii*-specific IgG and IgM as detected by the FMC-ELISA for IgM and a standard ELISA for IgG, but who possessed antibodies to rheumatoid factor/antinuclear factor, or one of the following infectious agents: Epstein-Barr Virus, Toxocara, Trichinella, cytomegalovirus, *Mycoplasma pneumoniae*. Group 4: 18 sera from 13 patients with previous discrepant recordings of *T.gondii*-specific IgM. Six of these sera were paired samples from three patients at the Flinders Medical Centre and the remaining 12 sera were from 10 patients who had been found to give discrepant results when tested using the MERCIA-ELISA, the SORIN-ELISA, and an tmmunosorbent agglutination test for *T.gondii*-specific IgM by Mr. D. Dickeson, Westmead Hospital, New South Wales.

Precision. To test the within assay precision of the ELISAs, four sera (one with an OD>1.0, one with 1.0>OD>0.6, one with 0.6>OD>0.2, one with OD<0.2) were tested nine times in one assay. To test the between assay precision of the ELISAs, one serum with an OD of >1.0 was tested in at least three assays for each ELISA.

Convenience of use. As these tests were being evaluated for their convenience of use in the routine clinical diagnosis of acute toxoplasmosis the operator made a subjective assessment of each ELISA on a scale of 1 (least convenient) to 5 (most convenient) based on 12 criteria.

Rheumatoid factor screening. Sera were tested for the presence of rheumatoid factor using a commercial kit (Rapi Tex RF New) according to the manufacturer's instructions (Behringwerke AG, Marburg, Germany).

Statistical analyses. Sensitivity, specificity and positive and negative predictive values were calculated as outlined by Griner et.al. (1981) according to the following formulae:

$$\text{sensitivity} = \frac{\text{true positives}}{\text{true positives} + \text{false negatives}};$$

$$\text{specificity} = \frac{\text{true negatives}}{\text{false positives} + \text{true negatives}};$$

$$\text{Positive predictive value} = \frac{\text{true positives}}{\text{true positives} + \text{false positives}};$$

$$\text{Negative predictive values} = \frac{\text{true negatives}}{\text{false negatives} + \text{true negatives}}$$

Their definitions are as follows:

Sensitivity, the probability that the assay will be positive when the disease is present;

Specificity, the probability that the assay will be negative when the disease is not present;

Positive predictive value, the probability that the disease is present when the assay is positive;

Negative predictive value, the probability that the disease is not present when the assay is negative.

Sensitivity was determined using group 1 of the serum panel, and specificity was determined using groups 2, 3 and 4 of the serum panel.

RESULTS

Positive sera—Group 1.

One commercial ELISA, the MERCIA-ELISA gave total correlation with the FMC-ELISA for the 38 T.gondii-specific IgM positive sera in this group. The SORIN-ELISA gave one false negative result, the ABBOTT-ELISA gave false negative results on two other sera, and the REC-ELISA gave false negative results on another six of the 31 sera tested (there was insufficient of 7 sera left to use for the REC-ELISA testing). The sensitivity values of each ELISA are contained in Table III.

Negative sera—Group 2.

This group of sera would appear to be simplest to test as they did not contain antibodies to T.gondii nor to other major infectious agents. Not surprisingly, therefore, all ELISAs gave specificity values of 100% for this group of sera.

Negative sera, positive for other infectious agents—group 3.

All of the ELISAs, with the exception of the ABBOTT-ELISA, gave negative predictive values of 100% with this group of sera which did not have T.gondii-specific IgG or IgM, but did have antibodies to one of a range of infectious agents. The ABBOTT-ELISA gave false positive results on a serum that was positive for Mycoplasma and a serum that was positive for antinuclear factor/rheumatoid factor, giving a specificity value of 86.7%. Both of these sera still gave positive results for T.gondii-specific IgM with this ELISA even after being treated for rheumatoid factor as described by the manufacturer.

Discrepant sera—Group 4.

Perhaps not surprisingly, this group of sera gave the most discordant results. Because the FMC-ELISA found these sera to all be negative for T.gondii-specific IgM, and the majority of ELISAs also found them to be negative, these sera were all taken to be negative for T.gondii-specific IgM. Eight of the sera (numbers 1,2,3,4,12,13,17 and 18) were found to contain rheumatoid factor, but this did not appear to obviously correlate with false positive results. The REC-ELISA found that only serum number 2 was positive (although sera number 3,5,7 and 8 were not tested by REC-ELISA as they were insufficient). The SORIN-ELISA found that sera number 14, and number 18 were positive, the MERCIA-ELISA found that sera numbers 1,2,3 and 4 were positive, and the ABBOTT-ELISA found that sera number 1,2,3,5,10,12,15 and 18 were positive. Even after treatment for rheumatoid factor as described in the ABBOTT-ELISA these 8 sera remained positive. These results gave specificity values of 92.9% (REC-ELISA), 88.9% (SORIN-ELISA), 77.8% (MERCIA-ELISA), and 50.0% (ABBOTT-ELISA), for this group of known discrepant sera.

The combined positive and negative predictive values and the sensitivity and specificity for all ELISAs are contained in Table III.

Precision.

From the results of the four sera used in the within assay analysis it appeared that, in general, the greater the amount of T.gondii-specific IgM in a serum, the smaller the coefficient of variation of the ELISA. The coefficients of variation for the four sera for each ELISA are contained in Table IV.

The between assay analysis of precision gave coefficients of variation as follows:

ABBOTT-ELISA—4.86%; SORIN-ELISA—8.1%; MERCIA-ELISA—8.0%; FMC-ELISA—7.8%; REC-ELISA—3.54%.

Convenience of use.

The assessment of convenience of use of each ELISA is contained in Table V.

TABLE III

Positive and negative predictive values, sensitivity and specificity for five ELISAs for the diagnosis of acute toxoplasmosis.

| Statistic | ELISA | | | | |
| --- | --- | --- | --- | --- | --- |
| | ABBOTT | MERCIA | SORIN | FMC | REC |
| Positive Predictive value | 76.6% | 90.5% | 94.9% | 100.0% | 96.1% |
| Negative Predictive value | 94.9% | 100.0% | 97.9% | 100.0% | 87.5% |
| Sensitivity | 94.7% | 100.0% | 97.4% | 100.0% | 80.6% |
| Specificity | 77.1% | 91.7% | 95.8% | 100.0% | 97.7% |

TABLE IV

Comparison of co-efficients of variation of five ELISAs for the diagnosis of acute toxoplasmosis on 4 different sera tested 9 times in the one assay.

| ELISA | Serum 1 (OD < 0.2) | 2 (0.2 < OD < 0.6) | 3 (0.6 < OD < 1.0) | 4 (OD > 1.0) |
|---|---|---|---|---|
| ABBOTT | 7.22% | 3.72% | 2.87% | 2.78% |
| FMC | 8.22% | 5.50% | 4.35% | 8.08% |
| MERCIA | 7.31% | ND[a] | 3.51% | 6.63% |
| SORIN | 8.00% | 6.11% | 4.74% | 4.43% |
| REC | ND | 18.99% | 15.04% | 4.82% |

[a]ND, not done

TABLE V

Convenience of use of five ELISAs for the diagnosis of acute toxoplasmosis.

| Parameter | ABBOTT | MERCIA | SORIN | FMC | REC |
|---|---|---|---|---|---|
| Number of serum dilution steps | 0 | 1 | 1 | 1 | 1 |
| Reciprocal of Serum dilution | 40 | 101 | 101 | 64 | 50 |
| Are controls treated the same as tests | Yes | No | No | Yes | Yes |
| Incubation time (hours) | 0.45 | 2.5 | 2.4 | 4.5 | 3.16 |
| Specimen type | s[a] | s | s, p[b] | s, p | s, p |
| Minimum sample volume used (μl) | 150 | 10 | 10 | 10 | 10 |
| Number of washes | NA[c] | 5 | 5 | 3 | 4 |
| Wavelength for reading (nm) | NA | 450 | 450 | 405 | 405 |
| Clarity of written instructions | 3 | 4 | 3 | NA | NA |
| Presentation of reagents | 5 | 5 | 4 | NA | NA |
| Protocol for removal of RF | Yes | No | No | NA | NA |
| Expression of results/ Interpretation of results | 5 | 4 | 2 | 4 | 4 |
| Overall assessment | 5 | 4 | 3 | 3 | 3 |

[a]serum
[b]plasma
[c]Not applicable

Although the ABBOTT-ELISA was the easiest test to use, and was very reproducible with all coefficients of variation being less than 7.3%, its specificity was the lowest of the ELISAs tested. These results appear to be in contrast to those of Schaefer et.al. (1989) who found a specificity of 98.7% for the ABBOTT-ELISA. However, they used an immunosorbent agglutination assay to differentiate discordant results. The coefficients of variation found here are comparable with those found for this ELISA by Schaefer et.al. (1989). although it had reduced specificity, the MERCIA-ELISA stands out as being the only commercial ELISA that gave 100% for negative predictive value and sensitivity. By contrast, Joynson et.al. (1989) had found that the sensitivity of this ELISA was low compared with some of the others they tested, none of which were available for the analysis reported here. The SORIN-ELISA was considered to give overall comparable satisfactory performance with regard to predictive values and specificity.

ELISAs using H4/GST or H11/GST, but not both, have been compared with the FMC-ELISA on another group of sera and gave a correlation of 58 (see Example 3). However, Srivastava et.al. (1989) found that a mixture of three recombinant polypeptides of *Plasmodium falciparum* significantly increased the sensitivity of their ELISAs, even when the single polypeptides were present at lower concentrations in the ELISA based on the mixture than in ELISAs based on the single recombinant polypeptides. Therefore, in the study reported here we used equal quantities of the recombinant fusion polypeptides mixed together as the antigen. Consistent with the findings of Srivastava et.al. (1989), the mixture of H4/GST and H11/GST used in the research reported here did appear to give better correlation with positive sera (sensitivity 80.6%). The REC-ELISA's positive predictive value was the lowest found for any ELISA. The coefficients of variation of 15% and 19% obtained with the REC-ELISA are high, but this may be associated with the avidity of the antibodies for the unique antigens used in the REC-ELISA. Antibody avidity increases with time after an antigenic challenge, and this fact has recently been used to diagnose acute toxoplasmosis via a low avidity IgG elution ELISA (Hedman et.al. 1989; Joynson et.al. 1990). Unlike the other ELISAs tested here, the REC-ELISA does not only detect *T.gondii*-specific IgM, because it uses an anti-IgG (heavy and light chain) conjugate. Hence, the success of the REC-ELISA may rest on the avidity of the H4/GST and H11/GST fusion polypeptides with either IgG and/or IgM-antibodies to *T.gondii* produced during the acute stages of infection. Nevertheless, REC-ELISAs such as that used here appear to be a promising advance in the serological diagnosis of acute toxoplasmosis.

REFERENCES

Abbas, A. M. A. (1976) *Bull. WHO* 36 344–346.

Bradford, (1976). *Analytical Biochemistry* 72, 248.

Burg, J. L. et. al. (1988). *J.Immunol.* 141, 3584–3591.

Burg, J. L. et.al. (1989). *J.Clin. Microbiol.* 27, 1787–1792.

Cesbron-Delaw, M. F. et.al., (1989). *Proc. Natl. Acad. Sci. (U.S.A.)*. 86, 7537–7541.

Chain, B. J. et.al., (1988). *Immunological Reviews* 106, 33.

Dahl, R. J. and Johnson, A. M. (1984). *Trans. R. Soc. Trop. Med. Hyg.* 78, 661.

Dubey, J. P. and Beattie, C. P. (1988). *CRC Press Inc. Florida,* "Toxoplasmosis of animals and man".

Frenkel, J. K. (1990). *J. Amer. Vet. Med. Assoc.* 186, 240.

Griner, P. F. et.al. (1981). *Ann. Int. Med.* 94:553–600.

Hedman, K. et.al. (1989). *J. Infect. Dis.* 159:736–740.

Helfman, D. M. et.al. (1983). *Proc. Natl. Acad. Sci. (U.S.A)*. 80, 31–35.

Helfman, D. M. et.al., (1984). *Focus* 6, 1–5.

Jakob-Hoff, R. M. and Dunsmore, J. D. (1983). *Aust. Vet. J.* 60, 217.

Johnson, A. M. et.al. (1983). *J. Parasitol.* 69, 459–464.

Johnson, A. M. et.al. (1985). *Pathology* 17:586–589.

Johnson, A. M. et.al. (1986). *Aust. J. Exp. Biol. Medi.Sci.* 64, 351–355.

Johnson, A. M. et.al. (1987). *Aust. NZ J.Med.* 17, 430–434.

Johnson, A. M. (1988). *Int. J. Parasitol.* 18, 865.

Johnson, A. M. et.al. (1989). *Gene* 85, 215–220.

Joynson, D. H. M. et.al. (1989). *J. Clin. Pathol.* 42: 653–657.

Joynson, D. H. M. et.al. (1990). *J. Clin. Pathol.* 43:1032–1033.

Julius, M. H. et.al. (1973). *Eur. J. Immunol.* 3, 645.

Kasper, L. H. et.al. (1984). *J. Immunol.* 132, 443.

Lunde, M. N. and Jacobs, L. (1983). *J. Parasitol.* 69, 219.

Nagel, S. D. and Boothroyd, J. C. (1988). *Mol. Biochem. Parasitol.* 29, 261–273.

Naot, Y. et.al. (1981). *J. Clin. Microbiol.* 14:73–78.

Prince, B. J. et.al. (1989). *Mol. Biochem. Parasitol.* 34, 3–14.

Rothbard, J. B. (1986). *Ann. Inst. Pasteur* 137E, 518–528.

Rothe, J. et.al. (1985). *Pathology* 17, 497.

Russo, D. M. et.al. (1985). *J. Immunol.* 143, 655–659.

Sambrook, J. et.al. (1989). Molecular Cloning: A Cold Spring Harbor Laboratory, Cold Laboratory Manual. Spring Harbor, N.Y.

Sanger, F. et.al. (1977). *Proc. Natl. Acad. Sci. (U.S.A.)*. 74, 5463–5467.

Schaefer, L. E. et.al. (1989). *J. Clin. Microbiol.* 27:2410–2413.

Smith, D. B. and Johnson, K. S. (1988). *Gene* 67, 31–40.

Srivastava, I. K. et.al. (1989). *Trans. R.Soc. Trop. Med. Hyg.* 83:317–321.

Strickland, G. T. et.al. (1975). *Clin. and Exp. Immunol.* 22, 167.

Tenter, A. M. and Johnson, A. M. (1990). *J.Immunoassay (in press)*.

Timmins, J. G. et.al. (1985). *Gene* 39, 89–93.

Voller, A. et.al. (1976). *J. Clin. Path.* 29, 150.

---

We claim:

1. A synthetic or recombinant polypeptide which specifically binds antibody which specifically binds 25 kDa H4 or 41 kDa H11 polypeptides of *Toxoplasma gondii*.

2. A synthetic or recombinant polypeptide according to claim 1, comprising an amino acid sequence as shown in FIG. 1A or FIG. 1B, or an antigenic fragment thereof which specifically binds anti-*T.gondii* antibody.

3. A synthetic or recombinant polypeptide which is a fused product comprising a first amino acid sequence which specifically binds antibody which specifically binds 25 kDa H4 or 41 kDa H11 polypeptides of *T. gondii*, and a second amino acid sequence fused thereto.

4. A synthetic or recombinant polypeptide according to claim 3, wherein the said second amino acid sequence comprises a β-galactosidase sequence or a glutathione-S-transferase sequence.

5. A synthetic or recombinant polypeptide according to claim 3, wherein said first amino acid sequence comprises an amino acid sequence as shown in FIG. 1A or FIG. 1B, or an antigenic fragment thereof which binds anti-*T. gondii* antibody.

6. A method for the detection of antibodies to *T. gondii* in a sample, wherein said sample is contacted with an antigen and binding of antibodies in said sample to said antigen is detected in a diagnostic immunoassay, wherein said antigen comprises a synthetic or recombinant polypeptide which specifically binds antibody which specifically binds 25 kDa H4 or 41 kDa H11 polypeptides of *T. gondii*.

7. A method according to claim 6, wherein said diagnostic assay is a radioimmunoassay.

8. A method according to claim 6, wherein said diagnostic immunoassay is an enzyme-linked immunosorbent assay.

9. A method according to claim 6, wherein said sample is a serum sample from a human or other animal patient.

10. A method according to claim 6, wherein said synthetic or recombinant polypeptide comprises a first amino acid sequence which specifically binds antibody which specifically binds 25 kDa H4 or 41 kDa H11 polypeptides of *T. gondii*, fused to a glutathione-S-transferase sequence.

11. A method according to claim 6, wherein said synthetic or recombinant polypeptide comprises an amino acid sequence as shown in FIG. 1A or FIG. 1B, or an antigenic fragment thereof which binds anti-*T. gondii* antibody.

12. A method according to claim 10, wherein said first amino acid sequence comprises an amino acid sequence as shown in FIG. 1A or FIG. 1B, or an antigenic fragment thereof which binds anti-*T.gondii* antibody.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 682 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..289

( x i ) SEQUENCE DESCRIPTION: SEQ ID NO:1:

```
GAA  TTC  CAA  GAG  GAA  ATC  AAA  GAA  GGG  GTG  GAG  GAA  CAC  AAG  CAT  GAA      48
Glu  Phe  Gln  Glu  Glu  Ile  Lys  Glu  Gly  Val  Glu  Glu  His  Lys  His  Glu
 1                    5                        10                       15

GAC  GAT  CCT  GAG  ATG  ACG  CGG  CTC  ATG  GTG  ACC  GAG  AAG  CAG  GAG  AGC      96
Asp  Asp  Pro  Glu  Met  Thr  Arg  Leu  Met  Val  Thr  Glu  Lys  Gln  Glu  Ser
                     20                       25                       30

AAA  AAT  TTC  AGC  AAG  ATG  GCG  AAA  TCC  CAG  AGT  TTT  AGC  ACG  CGA  ATC     144
Lys  Asn  Phe  Ser  Lys  Met  Ala  Lys  Ser  Gln  Ser  Phe  Ser  Thr  Arg  Ile
               35                       40                       45

GAA  GAG  CTC  GGG  GGA  TCC  ATT  TCG  TTT  CTA  ACT  GAA  ACG  GGG  GTC  ACA     192
Glu  Glu  Leu  Gly  Gly  Ser  Ile  Ser  Phe  Leu  Thr  Glu  Thr  Gly  Val  Thr
          50                       55                       60
```

```
ATG ATC GAG TTG CCC AAA ACT GCT AGT GAA CAT GAC ATG GAC CAA CTA        240
Met Ile Glu Leu Pro Lys Thr Ala Ser Glu His Asp Met Asp Gln Leu
 65                  70                  75                  80

CTC CAC GAT ATT CTC GCC GCA GTG GAG TCG TTG GGC TCG ACT CCG AGG T      289
Leu His Asp Ile Leu Ala Ala Val Glu Ser Leu Gly Ser Thr Pro Arg
                 85                  90                  95

GAAACTCGCA TAGATGCACG ACCCCAGTCG ATTTGCGAGT TATCGCGGAC CGTGACTAGC      349

AGCAGAGCTT TGTCAGCACG TATTTGTTCT TGTGGCTAAT ATTAGCAACA TGCCCGATGG      409

TTGTGGCATT CGGTATCGAT GTGAATAGTA GTGCAGTTTA TGTTCACGAA AGATGTTGTC      469

AAAGAGTCGT TGGAGCGGCA GAATGAGGCG ACGGTTGTAG GCCAGTTTGA TTTTGTGTAT      529

TAGTGGTACT AATGCAGAAC ATGCAAGGTG ATGCGCTTGC ATGGCTGAGG ATTCTCTTGG      589

AGCTTTTTGC TCAGCATCAG AAGCGCGAAC AAAGAATGTC CCTTTAAAGT GGTGACAACC      649

GCTGGAAAAA AAAAAAAAAA AAAAAGGAA TTC                                    682
```

( 2 ) INFORMATION FOR SEQ ID NO:2:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Glu Phe Gln Glu Glu Ile Lys Glu Gly Val Glu Glu His Lys His Glu
  1               5                  10                  15

Asp Asp Pro Glu Met Thr Arg Leu Met Val Thr Glu Lys Gln Glu Ser
             20                  25                  30

Lys Asn Phe Ser Lys Met Ala Lys Ser Gln Ser Phe Ser Thr Arg Ile
         35                  40                  45

Glu Glu Leu Gly Gly Ser Ile Ser Phe Leu Thr Glu Thr Gly Val Thr
     50                  55                  60

Met Ile Glu Leu Pro Lys Thr Ala Ser Glu His Asp Met Asp Gln Leu
 65                  70                  75                  80

Leu His Asp Ile Leu Ala Ala Val Glu Ser Leu Gly Ser Thr Pro Arg
                 85                  90                  95
```

( 2 ) INFORMATION FOR SEQ ID NO:3:

( i ) SEQUENCE CHARACTERISTICS:
        ( A ) LENGTH: 197 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..168

( x i ) SEQUENCE DESCRIPTION: SEQ ID NO:3:

```
GAA TTC CCC GCA AAG GCT GTC AAG GGA TTT GGT GGC ACC CGC ACT TCC        48
Glu Phe Pro Ala Lys Ala Val Lys Gly Phe Gly Gly Thr Arg Thr Ser
  1               5                  10                  15

ACG GCG CCT GCT GAG GCT GGA AAA ACG GAG TTG GAC GAC GGA TAT CGC        96
Thr Ala Pro Ala Glu Ala Gly Lys Thr Glu Leu Asp Asp Gly Tyr Arg
             20                  25                  30

CCG CCC CCA TTC AAC CCG CGA CCC TCA CCC TAC GCC GAG TTA TTG AAG        144
Pro Pro Pro Phe Asn Pro Arg Pro Ser Pro Tyr Ala Glu Leu Leu Lys
         35                  40                  45
```

```
GAT  TTG  GAA  AGA  ATG  CGC  AAA  GAG  TGACCGTGCT  GGGAAGCGAG  TTCGAATTC            197
Asp  Leu  Glu  Arg  Met  Arg  Lys  Glu
      50                          55
```

( 2 ) INFORMATION FOR SEQ ID NO:4:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Glu  Phe  Pro  Ala  Lys  Ala  Val  Lys  Gly  Phe  Gly  Gly  Thr  Arg  Thr  Ser
 1              5                        10                          15

Thr  Ala  Pro  Ala  Glu  Ala  Gly  Lys  Thr  Glu  Leu  Asp  Asp  Gly  Tyr  Arg
               20                        25                     30

Pro  Pro  Pro  Phe  Asn  Pro  Arg  Pro  Ser  Pro  Tyr  Ala  Glu  Leu  Leu  Lys
          35                        40                      45

Asp  Leu  Glu  Arg  Met  Arg  Lys  Glu
      50                          55
```